US012773328B2

(12) United States Patent
Vong et al.

(10) Patent No.: US 12,773,328 B2
(45) Date of Patent: Oct. 27, 2026

(54) STENT AND STENT DELIVERY DEVICE

(71) Applicant: Terumo Corporation, Tokyo (JP)

(72) Inventors: Shirley Vong, Tokyo (JP); Priscilla Tsai, Tokyo (JP); Cang Lam, Tokyo (JP); Ross Soltanian, Tokyo (JP); Greg Bak-Boychuk, Tokyo (JP); Tai D. Tieu, Tokyo (JP); Ponaka Pung, Tokyo (JP); Arnold Tuason, Tokyo (JP); Heather Griffith, Tokyo (JP)

(73) Assignee: Terumo Corporation, Tokyo (JP)

( * ) Notice: Subject to any disclaimer, the term of this patent is extended or adjusted under 35 U.S.C. 154(b) by 157 days.

(21) Appl. No.: 18/932,431

(22) Filed: Oct. 30, 2024

(65) Prior Publication Data

US 2025/0049593 A1 Feb. 13, 2025

Related U.S. Application Data

(63) Continuation of application No. 18/069,868, filed on Dec. 21, 2022, now Pat. No. 12,167,975, which is a
(Continued)

(51) Int. Cl.
*A61F 2/88* (2006.01)
*A61F 2/844* (2013.01)
(Continued)

(52) U.S. Cl.
CPC .............. *A61F 2/852* (2013.01); *A61F 2/844* (2013.01); *A61F 2/885* (2013.01); *A61F 2/90* (2013.01);
(Continued)

(58) Field of Classification Search
CPC .. A61F 2/852; A61F 2/844; A61F 2/86; A61F 2/885; A61F 2/90; A61F 2/966;
(Continued)

(56) References Cited

U.S. PATENT DOCUMENTS 4,130,904 A 12/1978 Whalen
5,037,427 A 8/1991 Harada
(Continued)

FOREIGN PATENT DOCUMENTS

EP 1885286 4/2013
EP 2632389 4/2013
(Continued)

OTHER PUBLICATIONS

European Patent Office, Extended European Search Report dated Jul. 27, 2022 in European Patent Application No. 22168276.8, 8 pages.

(Continued)

*Primary Examiner* — Ryan J. Severson
(74) *Attorney, Agent, or Firm* — Inskeep IP Group, Inc.

(57) ABSTRACT

In one embodiment according to the present invention, a stent is described having a generally cylindrical body formed from a single woven nitinol wire. The distal and proximal ends of the stent include a plurality of loops, some of which include marker members used for visualizing the position of the stent. In another embodiment, the previously described stent includes an inner flow diverting layer.

20 Claims, 32 Drawing Sheets

Related U.S. Application Data continuation of application No. 16/988,546, filed on Aug. 7, 2020, now Pat. No. 11,564,819, which is a continuation of application No. 16/414,689, filed on May 16, 2019, now Pat. No. 10,765,540, which is a continuation of application No. 15/247,714, filed on Aug. 25, 2016, now Pat. No. 10,335,297, which is a continuation of application No. 13/843,342, filed on Mar. 15, 2013, now Pat. No. 9,439,791.

(60) Provisional application No. 61/667,895, filed on Jul. 3, 2012, provisional application No. 61/618,375, filed on Mar. 30, 2012, provisional application No. 61/612,158, filed on Mar. 16, 2012.

(51) Int. Cl.

| | |
|---|---|
| ***A61F 2/852*** | (2013.01) |
| ***A61F 2/90*** | (2013.01) |
| ***A61F 2/966*** | (2013.01) |
| *A61F 2/82* | (2013.01) |
| *A61F 2/95* | (2013.01) |

(52) U.S. Cl.
CPC ........ *A61F 2/966* (2013.01); *A61F 2002/823* (2013.01); *A61F 2/9522* (2020.05); *A61F 2002/9528* (2013.01); *A61F 2002/9665* (2013.01); *A61F 2210/0014* (2013.01); *A61F 2210/0076* (2013.01); *A61F 2230/0021* (2013.01); *A61F 2230/005* (2013.01); *A61F 2230/0058* (2013.01); *A61F 2230/0067* (2013.01); *A61F 2250/0018* (2013.01); *A61F 2250/0023* (2013.01); *A61F 2250/0039* (2013.01); *A61F 2250/0098* (2013.01); *A61F 2310/00131* (2013.01)

(58) Field of Classification Search
CPC .............. A61F 2/9522; A61F 2002/823; A61F 2002/9528; A61F 2002/9665; A61F 2210/0014; A61F 2210/0076; A61F 2230/0021; A61F 2230/005; A61F 2230/0058; A61F 2230/0067; A61F 2250/0018; A61F 2250/0023; A61F 2250/0039; A61F 2250/0098; A61F 2310/00131; A61B 17/12113; A61B 17/12145; A61B 17/12168; A61B 2017/1205; A61L 31/022
See application file for complete search history.

(56) References Cited

U.S. PATENT DOCUMENTS

| | | | | |
|---|---|---|---|---|
| 5,383,925 | A | 1/1995 | Schmitt | |
| 5,492,532 | A | 2/1996 | Ryan et al. | |
| 5,702,418 | A | 12/1997 | Ravenscroft | |
| 5,741,325 | A | 4/1998 | Chaikof | |
| 5,741,332 | A | 4/1998 | Schmitt | |
| 5,846,259 | A | 12/1998 | Berthiaume | |
| 6,077,295 | A | 6/2000 | Limon | |
| 6,161,399 | A | 12/2000 | Jayaraman | |
| 6,342,068 | B1 | 1/2002 | Thompson | |
| 6,428,569 | B1 | 8/2002 | Brown | |
| 6,554,848 | B2 | 4/2003 | Boylan et al. | |
| 6,589,251 | B2 | 7/2003 | Yee et al. | |
| 6,592,549 | B2 | 7/2003 | Gerdts et al. | |
| 6,592,617 | B2 | 7/2003 | Thompson | |
| 6,623,518 | B2 | 9/2003 | Thompson et al. | |
| 6,652,574 | B1 | 11/2003 | Jayaraman | |
| 6,723,071 | B2 | 4/2004 | Gerdts et al. | |
| 6,733,521 | B2 | 5/2004 | Chobotov et al. | |
| 6,890,317 | B2 | 5/2005 | Gerdts et al. | |
| 6,942,688 | B2 | 9/2005 | Bartholf et al. | |
| 7,011,678 | B2 | 3/2006 | Tenerz | |
| 7,022,133 | B2 | 4/2006 | Yee et al. | |
| 7,108,716 | B2 * | 9/2006 | Burnside | A61L 31/044 623/1.13 |
| 7,115,109 | B2 | 10/2006 | Gerdts et al. | |
| 7,468,053 | B2 | 12/2008 | Gerdts et al. | |
| 7,763,011 | B2 | 7/2010 | Ortiz | |
| 7,867,267 | B2 | 1/2011 | Sullivan | |
| 8,100,935 | B2 | 1/2012 | Rosenbluth et al. | |
| 8,100,963 | B2 | 1/2012 | Roth | |
| 8,114,147 | B2 * | 2/2012 | Wood | A61F 2/90 623/1.15 |
| 8,118,859 | B2 * | 2/2012 | Tenne | A61B 17/12022 623/1.23 |
| 8,157,851 | B2 | 4/2012 | Andreas | |
| 8,409,267 | B2 * | 4/2013 | Berez | A61B 17/12 623/1.11 |
| 8,419,787 | B2 | 4/2013 | Yodfat et al. | |
| 8,425,584 | B2 | 4/2013 | Cully et al. | |
| 8,444,685 | B2 | 5/2013 | Gerdts et al. | |
| 8,597,276 | B2 | 12/2013 | Vongphakdy et al. | |
| 8,685,078 | B2 | 4/2014 | Gerdts et al. | |
| 8,778,008 | B2 | 7/2014 | Amplatz et al. | |
| 8,814,926 | B2 | 8/2014 | Fierens et al. | |
| 8,875,372 | B2 | 11/2014 | McHugo | |
| 9,072,623 | B2 | 7/2015 | Dorn | |
| 9,072,872 | B2 | 7/2015 | Asleson et al. | |
| 9,126,020 | B2 | 9/2015 | Farhangnia et al. | |
| 9,439,781 | B2 | 9/2016 | Vong et al. | |
| 9,439,791 | B2 | 9/2016 | Vong et al. | |
| 9,867,725 | B2 | 1/2018 | Tieu et al. | |
| 10,182,931 | B2 | 1/2019 | Pung et al. | |
| 10,335,297 | B2 | 7/2019 | Vong | |
| 10,463,515 | B2 | 11/2019 | Tieu | |
| 10,543,113 | B2 * | 1/2020 | Vong | A61F 2/852 |
| 10,765,540 | B2 | 9/2020 | Vong | |
| 11,291,566 | B2 * | 4/2022 | Tieu | D04C 1/06 |
| 11,351,046 | B2 * | 6/2022 | Tieu | A61F 2/88 |
| 11,564,819 | B2 * | 1/2023 | Vong | A61F 2/852 |
| 11,980,554 | B2 * | 5/2024 | Tieu | A61F 2/852 |
| 12,167,975 | B2 * | 12/2024 | Vong | A61F 2/852 |
| 2001/0018609 | A1 | 8/2001 | Smith | |
| 2001/0034549 | A1 | 10/2001 | Bartholf et al. | |
| 2001/0037141 | A1 | 11/2001 | Yee et al. | |
| 2001/0049547 | A1 | 12/2001 | Moore | |
| 2001/0049549 | A1 | 12/2001 | Boylan et al. | |
| 2001/0049554 | A1 | 12/2001 | Ruiz et al. | |
| 2001/0056299 | A1 | 12/2001 | Thompson | |
| 2002/0016597 | A1 | 2/2002 | Dwyer et al. | |
| 2002/0111668 | A1 | 8/2002 | Smith | |
| 2002/0120322 | A1 | 8/2002 | Thompson et al. | |
| 2002/0120323 | A1 | 8/2002 | Thompson et al. | |
| 2002/0133118 | A1 | 9/2002 | Gerdts et al. | |
| 2002/0151956 | A1 | 10/2002 | Chobotov et al. | |
| 2003/0149473 | A1 | 8/2003 | Chouinard et al. | |
| 2003/0199821 | A1 * | 10/2003 | Gerdts | A61F 2/95 606/195 |
| 2003/0199916 | A1 * | 10/2003 | Yee | A61F 2/95 606/198 |
| 2004/0098095 | A1 | 5/2004 | Burnside et al. | |
| 2004/0106977 | A1 * | 6/2004 | Sullivan | A61F 2/95 623/1.12 |
| 2004/0133264 | A1 * | 7/2004 | Moore | A61F 2/95 623/1.12 |
| 2004/0167601 | A1 * | 8/2004 | Gerdts | A61F 2/95 623/1.11 |
| 2005/0010279 | A1 | 1/2005 | Tenerz | |
| 2005/0137680 | A1 | 6/2005 | Ortiz et al. | |
| 2005/0171473 | A1 * | 8/2005 | Gerdts | A61F 2/962 623/1.11 |
| 2005/0217680 | A1 | 10/2005 | Callister | |
| 2007/0016282 | A1 * | 1/2007 | Gerdts | A61F 2/962 623/1.11 |
| 2007/0123973 | A1 | 5/2007 | Roth | |
| 2007/0168019 | A1 * | 7/2007 | Amplatz | A61F 2/07 623/1.18 |

(56) References Cited

U.S. PATENT DOCUMENTS

| | | | | |
|---|---|---|---|---|
| 2007/0250153 | A1* | 10/2007 | Cully | A61F 2/07 623/1.13 |
| 2007/0276470 | A1 | 11/2007 | Tenne | |
| 2008/0154357 | A1 | 6/2008 | Shalev | |
| 2009/0105808 | A1 | 4/2009 | Gerdts et al. | |
| 2009/0270974 | A1 | 10/2009 | Berez et al. | |
| 2009/0312834 | A1 | 12/2009 | Wood et al. | |
| 2011/0093002 | A1 | 4/2011 | Rucker et al. | |
| 2011/0137396 | A1 | 6/2011 | Dorn et al. | |
| 2011/0257720 | A1 | 10/2011 | Peterson et al. | |
| 2011/0270381 | A1 | 11/2011 | Fierens et al. | |
| 2011/0307049 | A1 | 12/2011 | Kao | |
| 2012/0259404 | A1* | 10/2012 | Tieu | A61F 2/88 623/1.15 |
| 2012/0310319 | A1* | 12/2012 | Tieu | A61F 2/945 623/1.4 |
| 2013/0060323 | A1* | 3/2013 | McHugo | A61F 2/90 623/1.18 |
| 2013/0079863 | A1* | 3/2013 | Dorn | A61F 2/2427 623/1.11 |
| 2013/0226308 | A1 | 8/2013 | Gerdts et al. | |
| 2013/0245745 | A1 | 9/2013 | Vong et al. | |
| 2013/0253474 | A1 | 9/2013 | Farhangnia et al. | |
| 2016/0361180 | A1 | 12/2016 | Vong et al. | |
| 2017/0112643 | A1 | 4/2017 | Cattaneo et al. | |
| 2017/0172766 | A1* | 6/2017 | Vong | A61F 2/852 |
| 2018/0008439 | A9* | 1/2018 | Tieu | A61F 2/852 |
| 2018/0036155 | A1* | 2/2018 | Tieu | A61F 2/90 |
| 2019/0269533 | A1 | 9/2019 | Vong et al. | |
| 2020/0030127 | A1* | 1/2020 | Tieu | A61F 2/88 |
| 2020/0368049 | A1 | 11/2020 | Vong et al. | |
| 2021/0244552 | A1* | 8/2021 | Tieu | A61F 2/88 |
| 2021/0346181 | A1* | 11/2021 | Tieu | A61F 2/852 |
| 2023/0132550 | A1* | 5/2023 | Vong | A61F 2/852 623/1.11 |
| 2024/0341982 | A1* | 10/2024 | Tieu | A61F 2/88 |
| 2025/0049593 | A1* | 2/2025 | Vong | A61F 2/852 |

FOREIGN PATENT DOCUMENTS

| | | | |
|---|---|---|---|
| JP | H11-197252 | A | 7/1999 |
| JP | 2004-519296 | A | 7/2004 |
| JP | 2008-173461 | A | 7/2008 |
| JP | 2009519061 | A | 5/2009 |
| JP | 6830054 | B2 | 2/2021 |
| WO | WO1994006373 | A1 | 3/1994 |
| WO | WO 03/011184 | A2 | 2/2003 |
| WO | WO 03/105728 | A1 | 12/2003 |
| WO | WO2006/026779 | A2 | 3/2006 |
| WO | WO2006/026779 | A3 | 3/2006 |
| WO | WO2006/133960 | A1 | 12/2006 |
| WO | WO2007068430 | A1 | 6/2007 |
| WO | WO 2008/118132 | A1 | 10/2008 |
| WO | WO2011049823 | A1 | 4/2011 |
| WO | WO2011/094527 | A1 | 8/2011 |
| WO | WO 2012/025247 | A1 | 3/2012 |

OTHER PUBLICATIONS

Japanese Patent Office, Office Action dated Dec. 28, 2021 with English translation in Japanese Patent Application No. JP 2020-176556, 6 pages.

Japanese Patent Office, Office Action dated Sep. 14, 2021 with English translation in Japanese Patent Application No. JP 2020-176556, 10 pages.

European Patent Office, "Decision to maintain the European patent in amended form (Art. 101(3)(a) EPC", in re Opposition by Pronovem Luxembourg s.a. to European Application No. 13761575.3, Jan. 23, 2020, 2 pages.

European Patent Office, "Termination of opposition proceedings of patent No. 13761575.3-1113 / 2825129 with maintenance of the patent", in re Opposition by Pronovem Luxembourg s.a. to European Application No. 13761575.3, Jan. 17, 2020, 1 page.

European Patent Office, "Maintenance of the patent with the documents specified in final decision", in re Opposition by Pronovem Luxembourg s.a. to European Application No. 13761575.3, Oct. 25, 2019, 1 page.

European Patent Office, "Minutes of Oral Hearing-Decision on Opposition", in re Opposition by Pronovem Luxembourg s.a. to European Application No. 13761575.3, Patent No. EP-B-2 825 129, Jun. 4, 2019, 145 pages.

European Patent Office, "Information re the result of oral proceedings", in re Opposition by Pronovem Luxembourg s.a. to European Application No. 13761575.3, Mar. 18, 2019, 24 pages.

Terumo Corporation (Propietor), "Observations by Proprietor to Notice of Opposition", in re Opposition by Pronovem Luxembourg s.a. to European Patent No. EP2825129, Jan. 18, 2019, 80 pages.

European Patent Office, "Summons to attend oral proceedings", in re Opposition by Pronovem Luxembourg s.a. to European Application No. 13761575.3, Aug. 8, 2018, 17 pages.

Microvention, Inc. (Propietor), "Reply by Proprietor to Notice of Opposition",in re Opposition by Pronovem Luxembourg s.a. to European Patent No. EP 2825129, Mar. 23, 2018, 26 pages.

Japanese Patent Office, JP Office Action mailed Jan. 25, 2017 in Japanese Patent Application No. JP 2015-500672, 18 pages (with English translation).

Pronovem Luxembourg s.a. (Opponent), "Notice of Opposition to a European Patent", in re Opposition by Pronoverm Luxumbourg s.a. to European Application No. 13761575.3, Patent No. EP2825129B1, Jan. 18, 2017, 16 pages.

WIPO, U.S. International Search Authority, International Search Report and Written Opinion mailed Jul. 26, 2013 in International Patent Application No. PCT/US2013/032636, 11 pages.

Henry, Michel et al., "Treatment of Renal Artery Aneurysm With the Multilayer Stent", *J Endovasc Ther* 2008, 15:231-236, 6 pages.

* cited by examiner

100

STENT AND STENT DELIVERY DEVICE

RELATED APPLICATIONS

This application is a continuation of and claims priority to U.S. patent application Ser. No. 18/069,868 filed Dec. 21, 2022 entitled Stent And Stent Delivery Device, which is a continuation of and claims priority to U.S. patent application Ser. No. 16/988,546 filed Aug. 7, 2020 entitled Stent And Stent Delivery Device (now U.S. Pat. No. 11,564,819 issued Jan. 31, 2023), which is a continuation of and claims priority to U.S. patent application Ser. No. 16/414,689 filed May 16, 2019 entitled Stent And Stent Delivery Device (now U.S. Pat. No. 1,065,540 issued Sep. 8, 2020), which is a continuation of U.S. patent application Ser. No. 15/247,714 filed Aug. 25, 2016 entitled Stent And Stent Delivery Device (now U.S. Pat. No. 10,335,297 issued Jan. 28, 2020), which is a continuation of U.S. patent application Ser. No. 13/843,342 filed Mar. 15, 2013 entitled Stent And Stent Delivery Device (now U.S. Pat. No. 9,439,791 issued Sep. 13, 2016), which claims benefit of and priority to U.S. Provisional Application Ser. No. 61/667,895 filed Jul. 3, 2012 entitled Stent, U.S. Provisional Application Ser. No. 61/618,375 filed Mar. 30, 2012 entitled Stent Deployment Device, and U.S. Provisional Application Ser. No. 61/612,158 filed Mar. 16, 2012 entitled Stent Deployment System, all of which are hereby incorporated herein by reference in their entireties.

BACKGROUND OF THE INVENTION

All of the following applications are hereby incorporated by reference in their entireties: U.S. Provisional Patent Application Ser. No. 61/422,604 filed Dec. 13, 2010 entitled Stent; U.S. Provisional Patent Application Ser. No. 61/425,175 filed Dec. 20, 2010 entitled Polymer Stent And Method Of Manufacture; International Patent Application No. PCT/US2010/061627, International Filing Date 21 Dec. 2010, entitled Stent; U.S. Provisional Patent Application Ser. No. 61/427,773 filed Dec. 28, 2010 entitled Polymer Stent And Method Of Manufacture 2; and U.S. Nonprovisional patent application Ser. No. 13/003,277 filed Jan. 7, 2011 entitled Stent.

The present invention relates to devices for the treatment of body cavities, such as the embolization of vascular aneurysms and the like, and methods for making and using such devices.

The occlusion of body cavities, blood vessels, and other lumina by embolization is desired in a number of clinical situations. For example, the occlusion of fallopian tubes for the purposes of sterilization, and the occlusive repair of cardiac defects, such as a patent foramen ovale, patent ductus arteriosis, and left atrial appendage, and atrial septal defects. The function of an occlusion device in such situations is to substantially block or inhibit the flow of bodily fluids into or through the cavity, lumen, vessel, space, or defect for the therapeutic benefit of the patient.

The embolization of blood vessels is also desired to repair a number of vascular abnormalities. For example, vascular embolization has been used to control vascular bleeding, to occlude the blood supply to tumors, and to occlude vascular aneurysms, particularly intracranial aneurysms.

In recent years, vascular embolization for the treatment of aneurysms has received much attention. Several different treatment modalities have been shown in the prior art. One approach that has shown promise is the use of thrombogenic microcoils. These microcoils may be made of biocompatible metal alloy(s) (typically a radio-opaque material such as platinum or tungsten) or a suitable polymer. Examples of microcoils are disclosed in the following patents: U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.; all of which are hereby incorporated by reference.

Stents have also been recently used to treat aneurysms. For example, as seen in U.S. Pat. No. 5,951,599—McCrory and U.S. Pub. No. 2002/0169473—Sepetka et al., the contents of which are incorporated by reference, a stent can be used to reinforce the vessel wall around the aneurysm while microcoils or other embolic material are advanced into the aneurysm. In another example seen in U.S. Pub. No. 2006/0206201—Garcia et al. and also incorporated by reference, a densely woven stent is placed over the mouth of the aneurysm which reduces blood flow through the aneurysm's interior and ultimately results in thrombosis.

In addition to flow diversion and occlusion, the present invention can also be used in applications where high coverage or low porosity is desirable. For example, when treating carotid artery stenosis with a stent, emboli or particulates may be dislodged during stent deployment or post-deployment dilatation. Since these emboli can become lodged in the brain and cause a stroke, it is desirable to provide a stent with low porosity to entrap the particulates. Another application of a high coverage stent is in areas of the body prone to thrombus formation such as in coronary bypass grafts (also called saphenous vein grafts or SVG) and arteries and veins in the lower extremities. Since the thrombus can dislodge and occlude downstream tissues, it is desirable to deploy a high coverage device of the instant invention to cover and/or entrap the thrombus to prevent it from migrating.

SUMMARY OF THE INVENTION

In one embodiment according to the present invention, a stent is described having a generally cylindrical body formed from a single woven nitinol wire. The distal and proximal ends of the stent include a plurality of loops, some of which include marker members used for visualizing the position of the stent.

In another embodiment according to the present invention, a delivery device is described, having an outer catheter member and an inner pusher member disposed in a passage of the catheter. The distal end of the pusher member includes a distal and proximal marker band that is raised above the adjacent portions of the pusher member body. The previously described stent can be compressed over the distal marker band such that the stent's proximal loops and proximal marker members are disposed between the distal and proximal marker bands on the pusher member.

In one example, the delivery device can be used to deliver the previously described stent over an opening of an aneurysm. The aneurysm is preferably first filled with microcoils or embolic material either before or after delivery of the stent.

In another embodiment according to the present invention, a dual layer stent is described having an outer anchoring stent similar to the previously described stent and a discrete inner mesh layer formed from a plurality of woven members. The proximal end of the outer stent and the inner stent are connected together by connecting members or crimping, allowing the remaining portions of the outer anchoring stent and inner mesh layer to independently change in length as each begins to expand in diameter. Alternately, the inner mesh layer may only extend along a portion of the length of outer stent and may be symmetrically or asymmetrically positioned between the out stent's distal and proximal ends.

In one example, the dual layer stent can be delivered over the opening of an aneurysm to modify the flow of blood that enters the aneurysm. As the blood flow into the aneurysm becomes stagnant, a thrombosis forms to block up the interior aneurysm space.

In another embodiment according to the present invention, a single or dual layer stent can be created by polymerizing a prepolymer liquid inside a tube, syringe or similar structure. Patterns can be created in the polymer structure via a pre-patterned mandrel on which the polymer structure is polymerized or by cutting the polymer structure after polymerization.

In another embodiment according to the present invention, a dual-layer stent is connected at multiple locations along its length. For example, a tantalum wire can be woven between both layers, maintaining the layers in close proximity to each other. Both layers of the stent may be braided or woven at the same braid angle (i.e., picks per inch) which allows both layers to contract in length by the same amount and rate during expansion.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
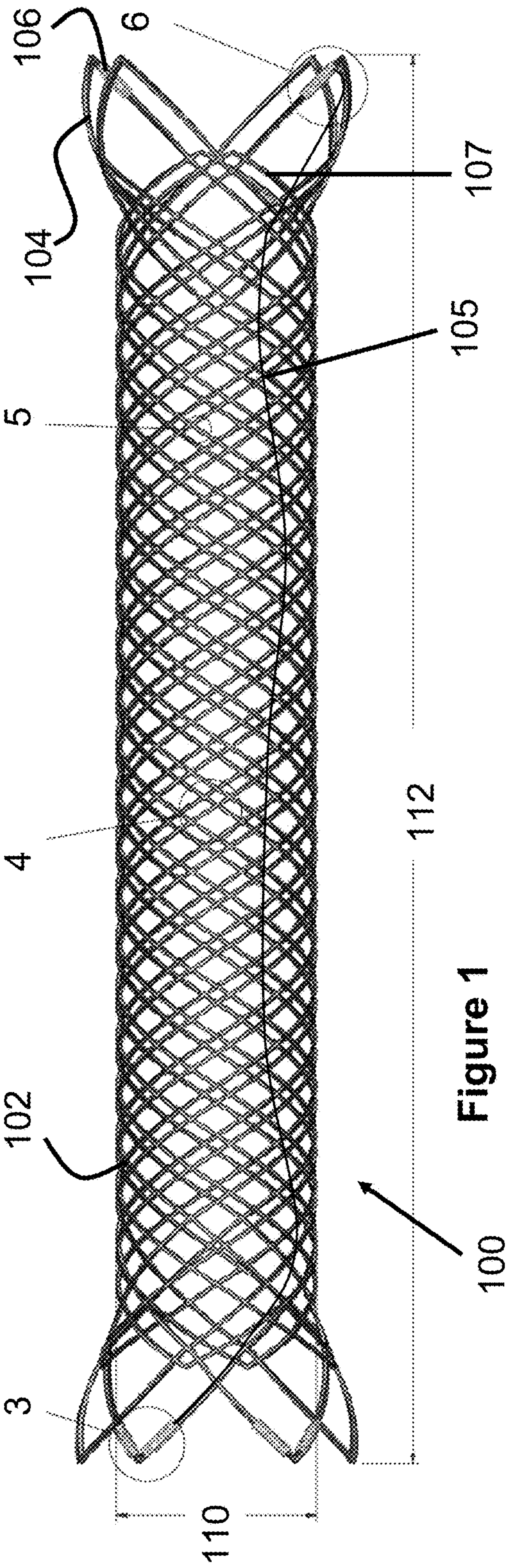
FIG. 1 illustrates a side view of a stent according to a preferred embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 illustrates a stent 100 according to a preferred embodiment of the present invention. The stent 100 is woven or braided together from a single wire 102 to form a generally cylindrical shape with a plurality of loops 104 around the perimeter of both ends of the stent 100.

Figure 5:
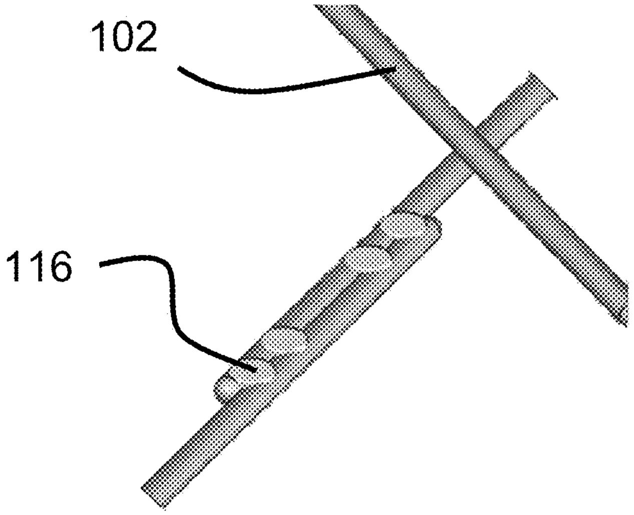
FIG. 5 illustrates a magnified view of area 5 in FIG. 1.

As seen in area 5 in FIG. 1 and in FIG. 5, the ends of the single wire 102 can be connected to each other via welding (see welded region 116), bonding agents or a similar adhesive mechanism. Once the ends are welded or bonded, the wire 102 has no "free" ends.

Each of the loops 104 may contain one or more coil members 106. Preferably, the coil members 106 are disposed around the wire 102 of the loops 104 which, as discussed in greater detail below, denote the proximal and distal ends of the stent 100. Additionally, these coil members 106 may provide additional anchoring force within a delivery device as described in greater detail below.

In one example, a distal end of the stent 100 includes at least two loops 104 with two coil members 106 each and a proximal end of the stent 100 includes at least two loops 104 with one coil member 106 each. However, it should be understood that the stent 100 can include any number of coil members 106 on any number of loops 104.

Preferably, these coil members 106 are positioned near a center area of the loop 104, such that when the stent 100 is in a collapsed state, the coil members 106 are positioned near the very distal or very proximal end of the stent 100.

Figure 3:
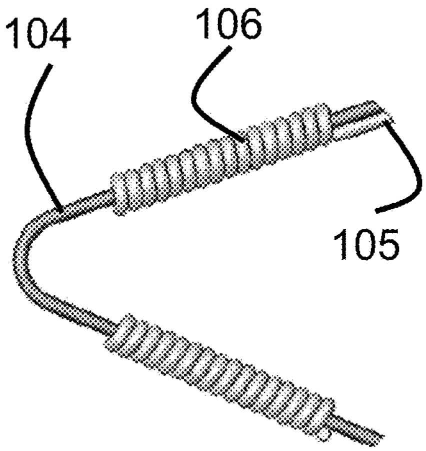
FIG. 3 illustrates a magnified view of area 3 in FIG. 1.
Figure 4:
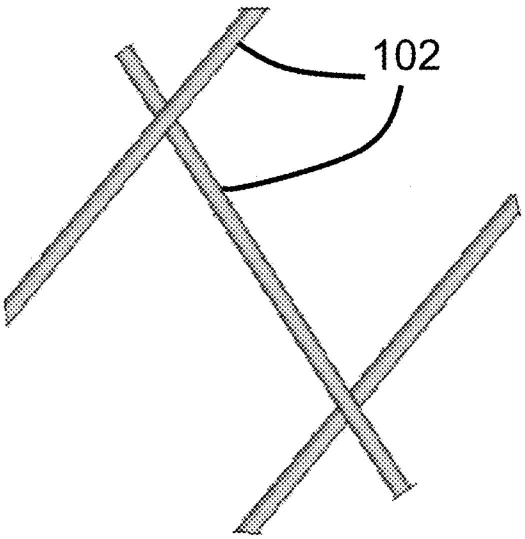
FIG. 4 illustrates a magnified view of area 4 in FIG. 1.
Figure 6:
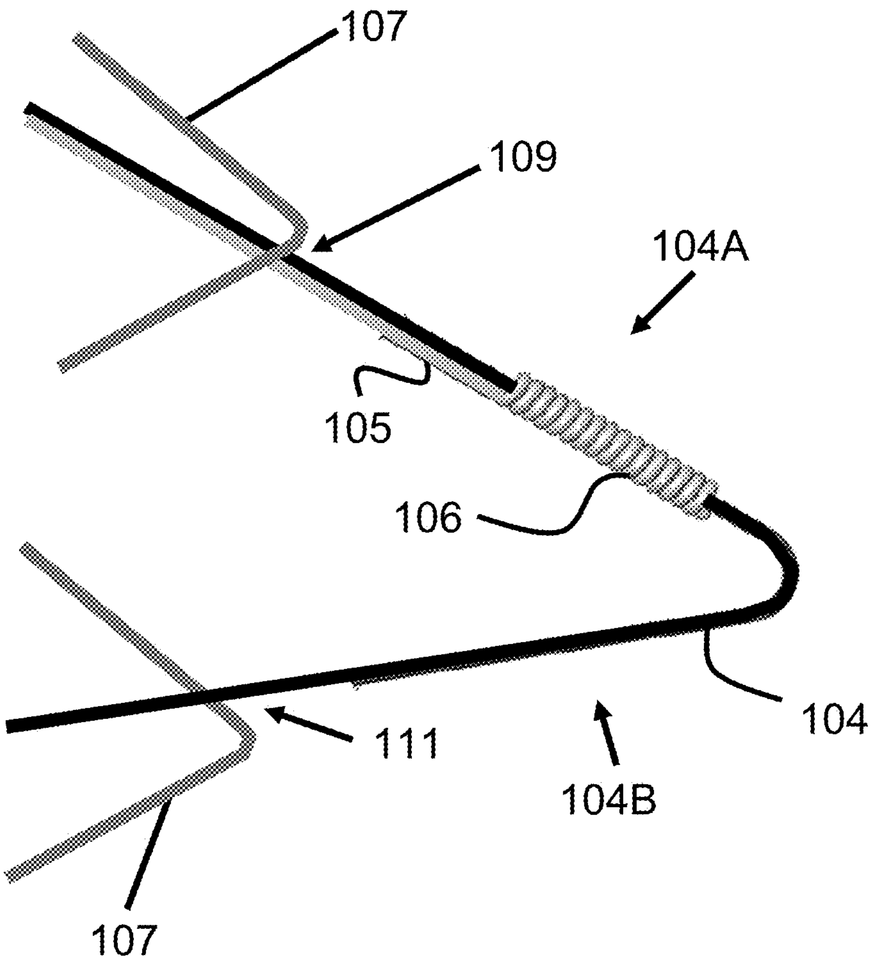
FIG. 6 illustrates a magnified view of area 6 in FIG. 1.
Figure 6A:
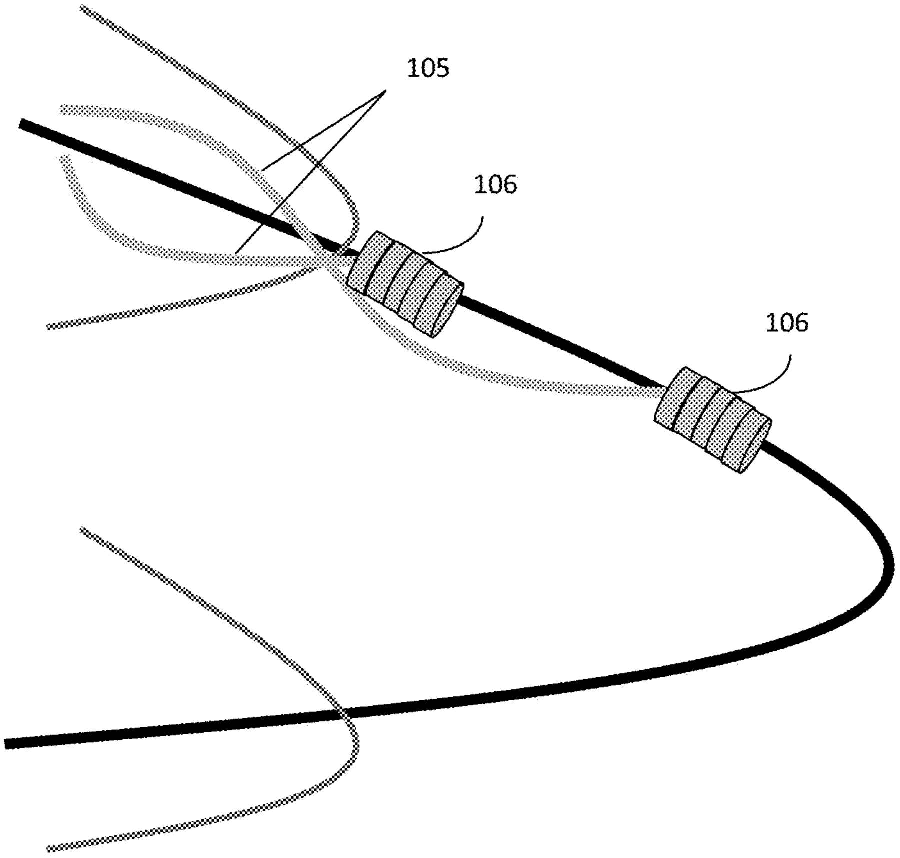
FIG. 6A illustrates an alternate view of area 6 in FIG. 1 have two coils formed by different strands of wire.

Preferably, each coil member 106 is composed of a wire 105 wound around a portion of the loop 104. Each coil member 106 can be composed of a discrete wire 105 (as seen in FIG. 3) or a single wire 105 can form multiple coil members 106 (as seen in FIGS. 1, 3 and 6). In the present preferred embodiment, some coil members 106 are composed of discrete sections of wire 105 while other coil members 106 on either end are formed from the same, continuous wire 105. As seen in FIG. 1, the wire 105 can connected to coil members 106 on each end of the stent 100 by being located within the inner portion or lumen of the stent 100. Alternately, the wire 105 may be woven into the wires 102 of the stent 100.

In another embodiment, wire 105 can be composed of two or more constituent wire elements which are wound together to produce wire 105. Utilizing two or more twisted wires to create element 105 can increase the flexibility of wire 105, by lowering the bend radius and thus increasing the overall curvature/flexibility. Increased flexibility may aid in collapsibility and trackability of the device.

When multiple wires are wound together to produce wire 105, each constituent wire element may individually wind at the proximal and distal ends of the stent to produce coils 106 in series. Thus one of the constituent wire elements can be wound to form one coil 106, followed by another one of the constituent wire elements wound into a subsequent coil 106.

Preferably, the wire 105 of the coil members 106 is composed of a radiopaque material such as tantalum or platinum. The wire 105 preferably has a diameter of about 0.00225".

Alternately, the coil members 106 may be a radiopaque sleeve that is disposed on and adhered to the loop 104.

In one embodiment, the loops 104 on the proximal end of the stent 100 have one coil 106 on each side of the loop 104 (as seen in FIG. 3) while the distal end of the stent 100 includes only one coil 106 on one side of each loop 104 (as seen in FIG. 6).

Preferably, the weaving pattern of the stent 100 prevents the distal coils 106 from being exposed or "sticking up" from an outer diameter of the stent 100 during retraction. Hence, if the user decides to retract the stent 100 back into the catheter for repositioning and redeployment, the distal coils 106 will not catch or contact the distal edge of the catheter, thereby minimizing damage to the stent 100 that might otherwise occur during retraction.

One specific technique for minimizing the exposure of the distal coils 106 during retraction is to weave the stent 100 such that portions of the wire 102 overlap (i.e., are positioned at a greater outer diameter position) than the side of the loop 104 with coil 106. As seen in FIG. 6, some smaller, minor loops 107 are woven to overlap a first side 104A of the loop 104 that includes the coil 106 (see location 109) while other minor loops 107 are woven underneath a second side 104B of the loop 104 (see location 111).

As a user retracts the stent 100 back into the catheter, the minor loops 107 move inward (i.e., towards the center of the stent's passage) as the stent 100 compresses in diameter, thereby inwardly pressing on the first side 104A of the loop 104. In this respect, the minor loops 107 exert inward or compressive force on the first side 104A of the loop 104. This configuration ensures that the first side 104A of the loop 104 and therefore the coil 106 is not positioned at an outermost diameter of the stent 100 during retraction and therefore reduces the likelihood of the coils 106 of catching or hooking on to the distal end of the deployment catheter.

Figure 2:
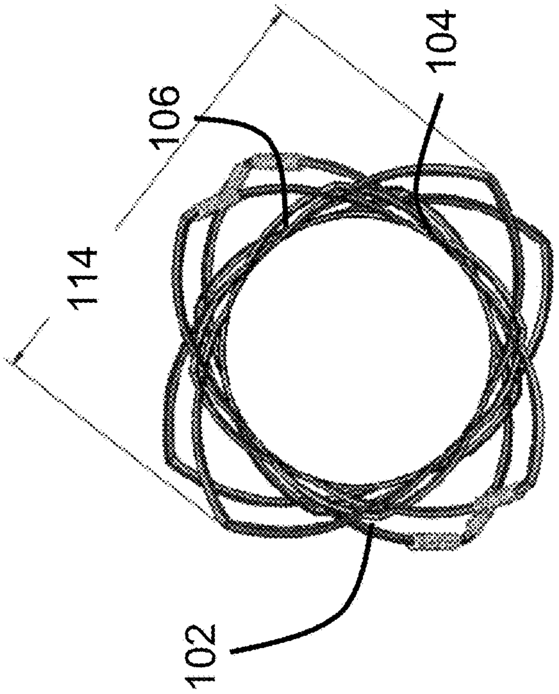
FIG. 2 illustrates a front view of the stent of FIG. 1.

As seen best in FIG. 1 and FIG. 2, the loops 104 are flared or biased to an outer diameter 114 when fully expanded relative to the diameter of the main body of stent 100. These loops 104 can also expand to a diameter that is even with or smaller than that of the main body.

Figure 9:
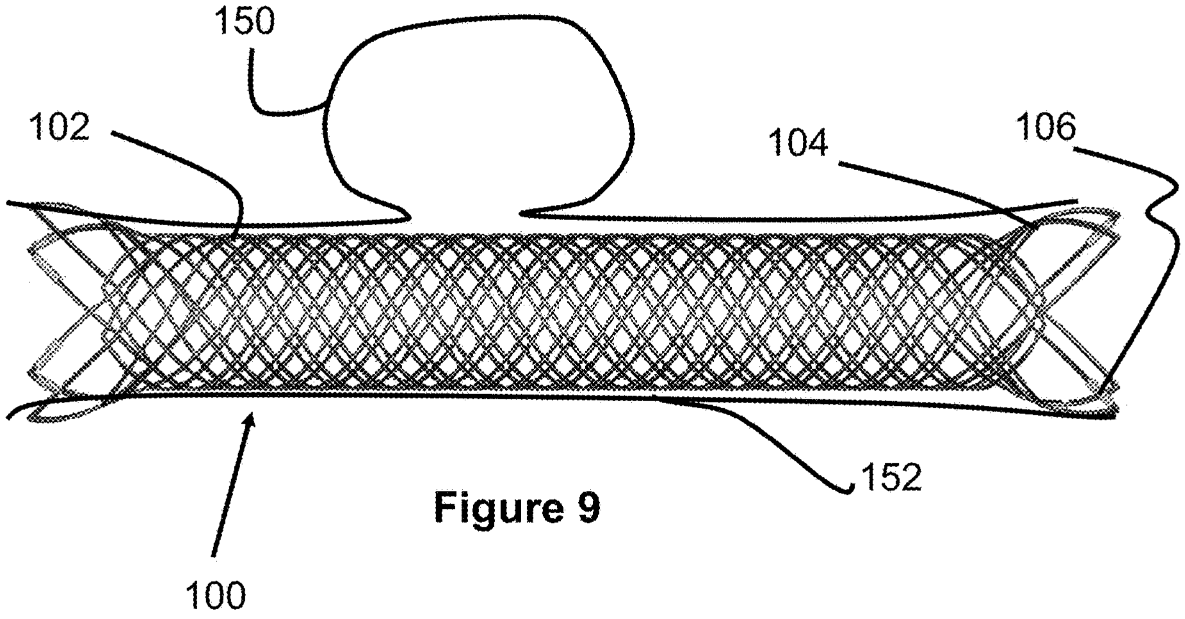
FIG. 9 illustrates the stent of FIG. 1 positioned over the opening of an aneurysm.

The stent 100 preferably has a diameter 110 sized for a vessel 152 in the human body, as seen in FIG. 9. More preferably, the diameter 110 is between about 2 mm and 10 mm. The length of the stent 100 is preferably sized to extend beyond the mouth of an aneurysm 150 as also seen in FIG. 9. More preferably, the length of the stent 100 is between about 5 mm and 100 mm.

Figure 7:
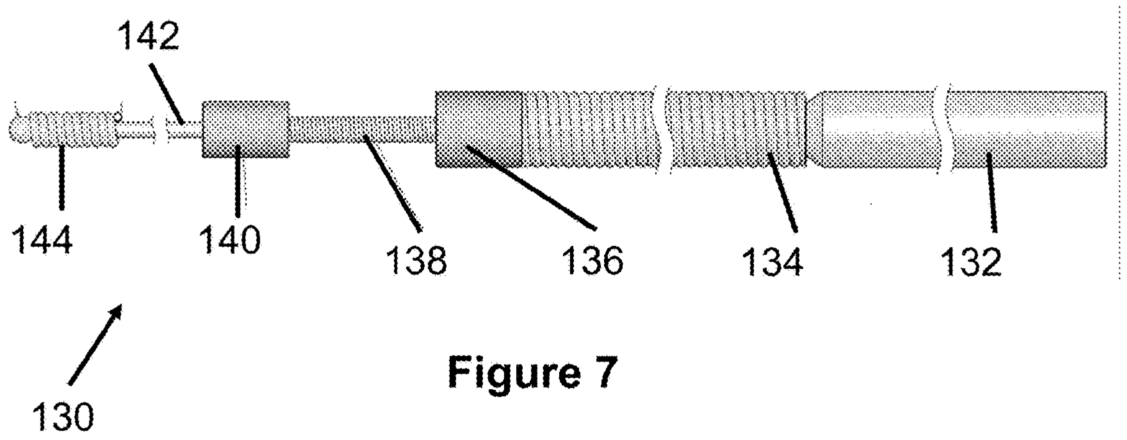
FIG. 7 illustrates a side view of a pusher member according to a preferred embodiment of the present invention.
Figure 8:
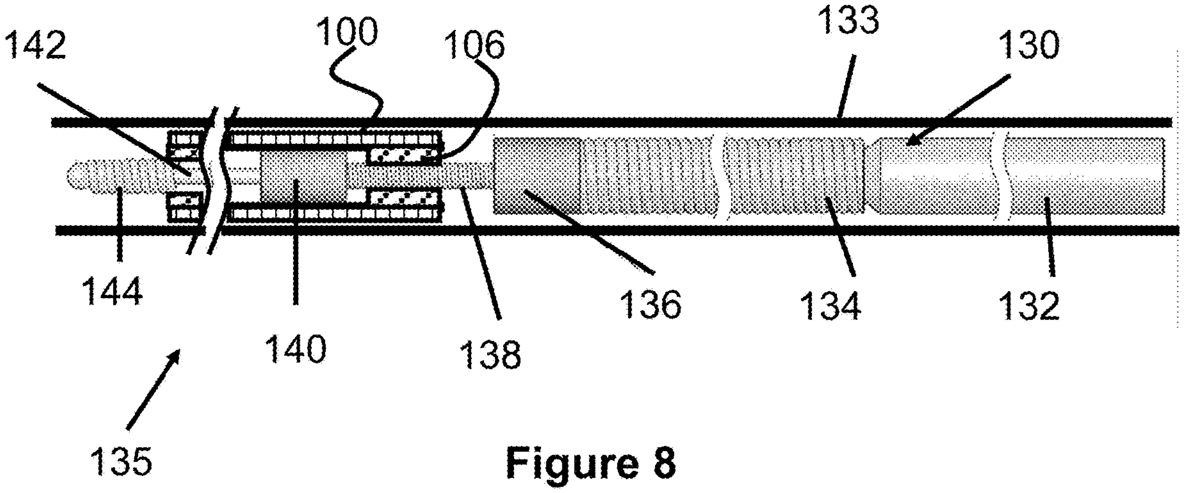
FIG. 8 illustrates a partial cross sectional view of the pusher member of FIG. 7 having the stent of FIG. 1 compressed over its distal end and being positioned in a catheter.

FIGS. 7 and 8 illustrate a delivery system 135 according to the present invention which can be used to deliver the stent 100. A catheter or sheath 133 is positioned over a delivery pusher 130, maintaining the stent 100 in its compressed position. Once the distal end of the sheath 133 has achieved a desired target location (i.e., adjacent an aneurysm 150), the sheath 133 can be retracted to release the stent 100.

The delivery pusher 130 is preferably composed of a core member 132, which tapers in diameter near its distal end (made from nitinol). A proximal area of the tapered end of the core member 132 includes a larger diameter first wire coil 134 that is preferably made from stainless steel and welded or soldered in place on the core member 132. Distal to the coiled wire is a first marker band 136 that is fixed to the core member 132 and preferably made from a radiopaque material such as platinum.

A smaller diameter second wire coil 138 is located distal to the marker band 136 and is preferably made from stainless steel or plastic sleeve. A second marker band 140 is located distal to the second wire coil 138 and is also preferably made from a radiopaque material such as platinum. Distal to the second marker band 140 is a narrow, exposed section 142 of the core member 132. Finally, a coiled distal tip member 144 is disposed on the distal end of the core member 132 and is preferably composed of a radiopaque material such as platinum or tantalum.

In one example, the inner diameter of the sheath 133 is about 0.027" and about 1 meter in length. The delivery pusher 130 is also about 2 meters in length. The sections of the delivery pusher 130 preferably have the following diameters: the proximal region of the core member 132 is about 0.0180 inch, the first wire coil 134 is about 0.0180 inch, the first marker band 136 is about 0.0175 inch, the second wire coil 138 is about 0.0050 inch, the second marker band 140 is about 0.0140 inch, the distal core member section 142 is about 0.003 inch, and the distal tip member 144 is about 0.0100 inch. The sections of the delivery pusher 130 preferably have the following lengths: the proximal region of the core member 132 is about 1 meter, the first wire coil 134 is about 45 cm, the first marker band 136 is about 0.020 inch, the second wire coil 138 is about 0.065 inch, the second marker band 140 is about 0.020 inch the distal core member section 142 is about 10 cm, and the distal tip member 144 is about 1 cm.

As seen in FIG. 8, the stent 100 is compressed over the distal end of the delivery pusher 130 such that the coil members 106 on the proximal end of the stent 100 are positioned between the first marker band 136 and the second marker band 140. Preferably, the proximal coil members 106 are not in contact with either marker band 136 or 140 and are maintained via frictional forces between the sheath 133 and the second coiled area 138.

When the distal end of the delivery pusher has reached an area adjacent a desired target location (e.g., near an aneurysm), the sheath 133 is retracted proximally relative to the delivery pusher 130. As the sheath 133 exposes the stent 100, the stent 100 expands against the walls of the vessel 152, as seen in FIG. 9.

The stent 100 can also be retracted (if it was not fully deployed/released) by retracting the pusher 130 in a proximal direction, thereby causing the marker band 140 to contact the proximal marker bands 106, pulling the stent 100 back into the sheath 133.

In one example use, the stent 100 can be delivered over the opening of an aneurysm 150 after embolic devices or material, such as embolic coils, have been delivered within the aneurysm 150. In this respect, the stent 100 helps prevent the treatment devices from pushing out of the aneurysm 150 and causing complications or reducing efficacy of the treatment.

In one example, the wire 102 is composed of a shape-memory elastic material such as nitinol between about 0.001 inch and 0.010 inch in diameter.

The wire 102 may also vary in diameter over the length of the stent 100. For example, the diameter of the wire 102 near the proximal and distal ends may be thicker than that of the middle portion of the stent 100. In another example, the proximal and distal ends may be thinner than the middle portion. In another example, the diameter of the wire 102 may alternate between larger and smaller diameters along the length of the stent 100. In yet another example, the diameter of the wire 102 may gradually increase or decrease along the length of the stent 100. In yet another example, the loops 104 may be composed of wire 102 having a larger or smaller diameter than that of the wire 102 comprising the main body of the stent 100. In a more detailed example, the diameter of the wire 102 of the loops 104 may be about 0.003 inch while the wire 102 of the body of the stent 100 may be about 0.002 inch.

In yet another example, select areas of the wire 102 may have a reduced thickness where the wire 102 may cross over another section in a compressed and/or expanded configuration of the stent 100. In this respect, the thickness of the stent 100 can be effectively reduced in certain configurations. For example, if sections of the wire 102 were reduced at areas where the wire 102 overlapped when in a compressed configuration, the overall profile or thickness of the stent 100 can be reduced, allowing the stent 100 to potentially fit into a smaller delivery catheter.

This variation in diameter of the wire 102 can be achieved by electropolishing, etching or otherwise reducing portions of the assembled stent 100 to cause a diameter reduction. Alternately, regions of the wire 102 can be reduced prior to being wound or woven into the shape of the stent 100. In this respect, a desired weaving pattern can be determined, the desired post-weaving, reduced-diameter regions can be calculated and reduced, and finally the stent 100 can be woven with the modified wire 102.

In another variation, the pre-woven wire 102 can be tapered along a single direction and woven together to form the stent 100.

Figure 10:
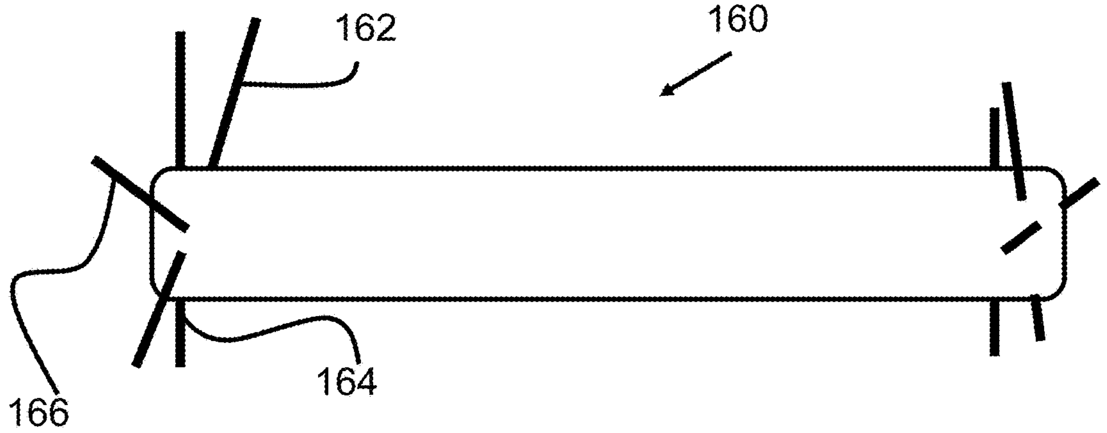
FIG. 10 illustrates a side view of a mandrel according to the present invention that can be used to create the stent of FIG. 1.

In one example preparation, a 0.0035 inch diameter nitinol wire is wound or woven over a mandrel 160. As seen in FIG. 10, the mandrel 160 may have three pins 162, 164, 166 extending through each end, such that a portion of each end of each pin extends out from the body of the mandrel 160. The wire 102 begins at one pin, and then is wound 3.0625 revolutions clockwise around the body of the mandrel 160. The wire 102 is bent around a nearby pin, then wound 3.0625 revolutions clockwise back towards the other side of the mandrel 160, passing over and under the previously wound section of wire 102. This process is repeated until eight loops are formed on each end.

In another example, the mandrel 160 may have 8 pins and the wire 102 is wound 2.375 revolutions. In another example, the mandrel 160 may have 16 pins and the wire 102 is wound 3.0625 revolutions. In yet another example, the mandrel may have between 8 and 16 pins and is wound between 2.375 and 3.0625 revolutions.

Once wound, the stent 100 is heat-set on the mandrel 160, for example, at about 500° C. for about 10 minutes. The two free ends of the nitinol wire can be laser welded together and electro-polished such that the final wire diameter is about 0.0023 inch.

Finally, the radiopaque wire 105 of about 0.00225 inch in diameter is wound onto different areas of the stent loops 104, forming coil members 106. Preferably, the wire 105 is wound for about 0.04 inch in length to create each coil member 106.

In another embodiment, the stent 100 can be formed from a plurality of discrete wires instead of a single wire 102. The ends of this plurality of wires can be left free or can be welded, adhered or fused together for form loops 104. In another embodiment, the stent 100 can be formed by laser cutting, etching, machining or any other known fabrications methods.

The wire 102 is preferably composed of a shape memory metal such as Nitinol. Optionally, this shape memory metal can include a variety of different therapeutic coatings or a hydrogel coating that swells or expands when exposed to blood. The wire 102 can also be composed of a biocompatible polymer material (e.g., PET) or from a hydrogel material.

Figure 11:
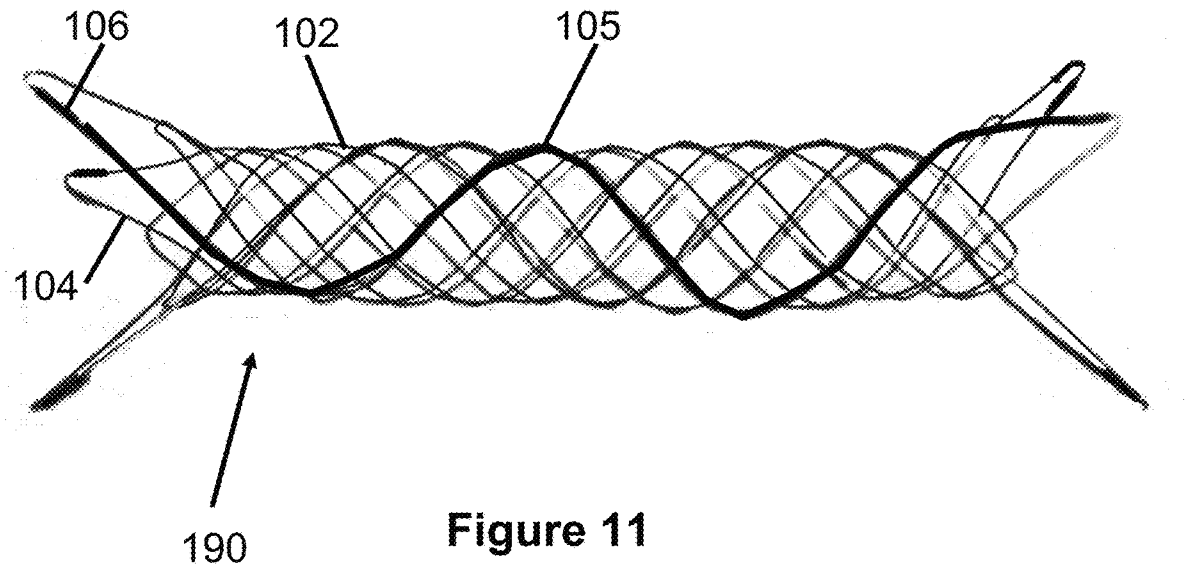
FIG. 11 illustrates a side view of a stent according to a preferred embodiment of the present invention.

FIG. 11 illustrates an embodiment of a stent 190 that is similar to the previously described stent 100, except that each end of the stent 190 includes three loops 104 instead of the four loops 104 of the previous stent 100. Additionally, the radiopaque wire 105 that form each of the coils 106 is also preferably woven into the stent 190, connecting at least some of the coils 104 on each end of the stent 190. Finally, the wire 102 is woven back and forth about 12 times along the length of the stent 190.

Figure 12:
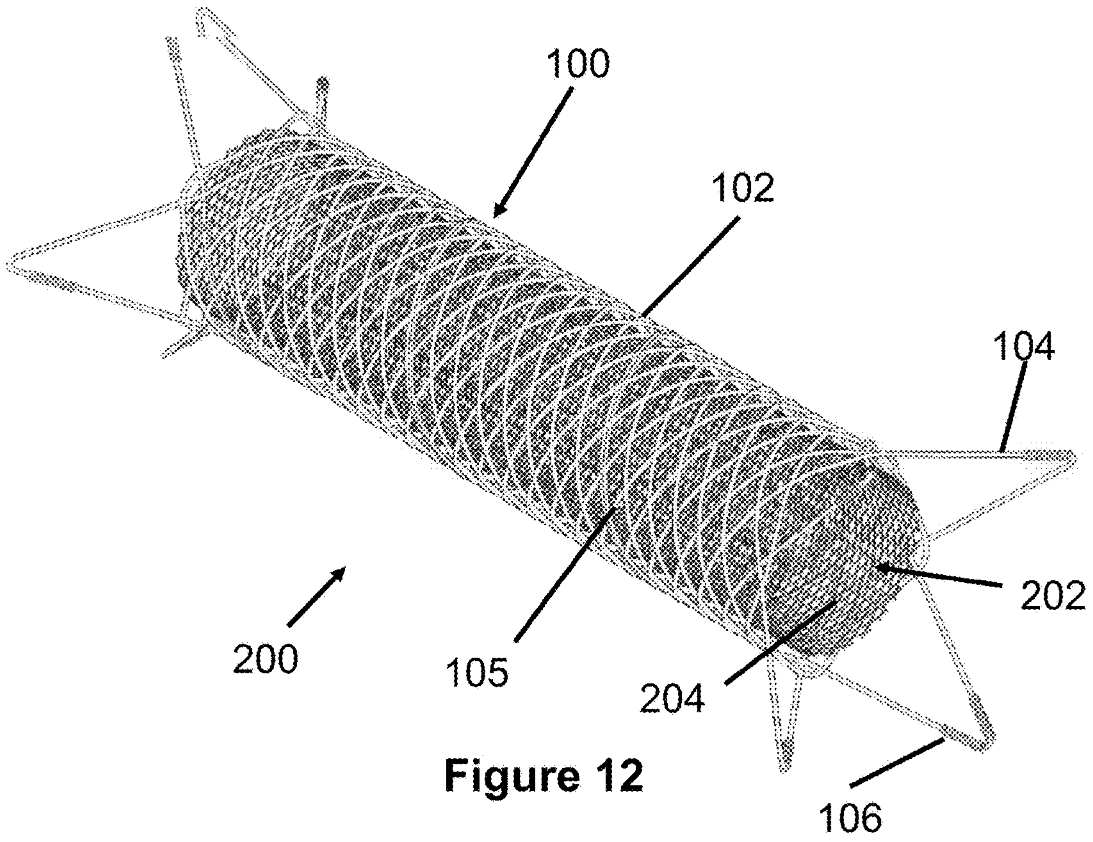
FIGS. 12-14 illustrate various views of a dual layer stent according to a preferred embodiment of the present invention.

FIG. 12 illustrates a preferred embodiment of a dual layer stent 200 according to the present invention. Generally, the dual layer stent 200 includes an outer anchoring stent 100 that is similar to the previously described stent 100 seen in FIGS. 1-9. The dual layer stent 200 also includes an inner flow-diverting layer 202 that is disposed within the inner lumen or passage of the anchoring stent 100.

Often, stents with relatively small wires do not provide adequate expansile forces and therefore do not reliably maintain their position at a target location. Additionally, prior art woven stents created with many wires can have free ends that can poke or damage a patient's vessel. In contrast, larger wires are difficult to weave tightly enough (i.e., large spaces between adjacent wires) to modify blood flow at a desired location. The stent 200 seeks to overcome these disadvantages by including both the larger wire braid anchoring stent 100 to provide a desired anchoring force and the smaller wire braid flow-diverting layer 202 to divert blood.

In one example, the flow-diverting layer 202 is composed of at least 32 wires 204 that are between about 0.0005 to about 0.002 inch in diameter and made from a memory elastic material such as nitinol. These wires 204 are woven or braided together in a tubular shape having a pore size less than 0.010 inch. Preferably, this braiding is achieved with a braiding machine, which is known in the art and can braid the wires 204 in a regular pattern such as a diamond shaped pattern.

The flow-diverting layer 202 can have areas of its wire 204 that have a reduced diameter, similar to the patterns and techniques previously described with regard to the wire 102 of the stent 100. Additionally, the flow-diverting layer 202 can be formed by laser cutting or etching a thin tube.

In the present example, the distal and proximal ends of the flow-diverting layer 202 are perpendicular relative to the length of the layer 202. However, these ends may also be angled relatively to the length of layer 202 in a matching, opposite or irregular angular configuration.

Figure 13:
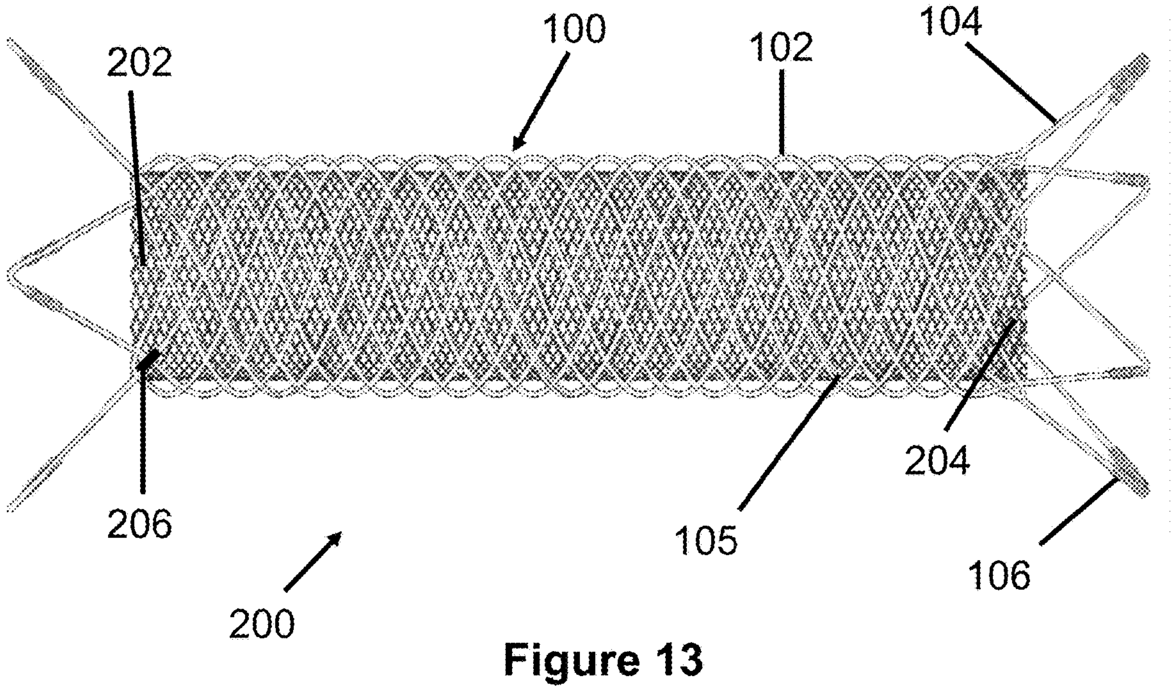
Figure 14:
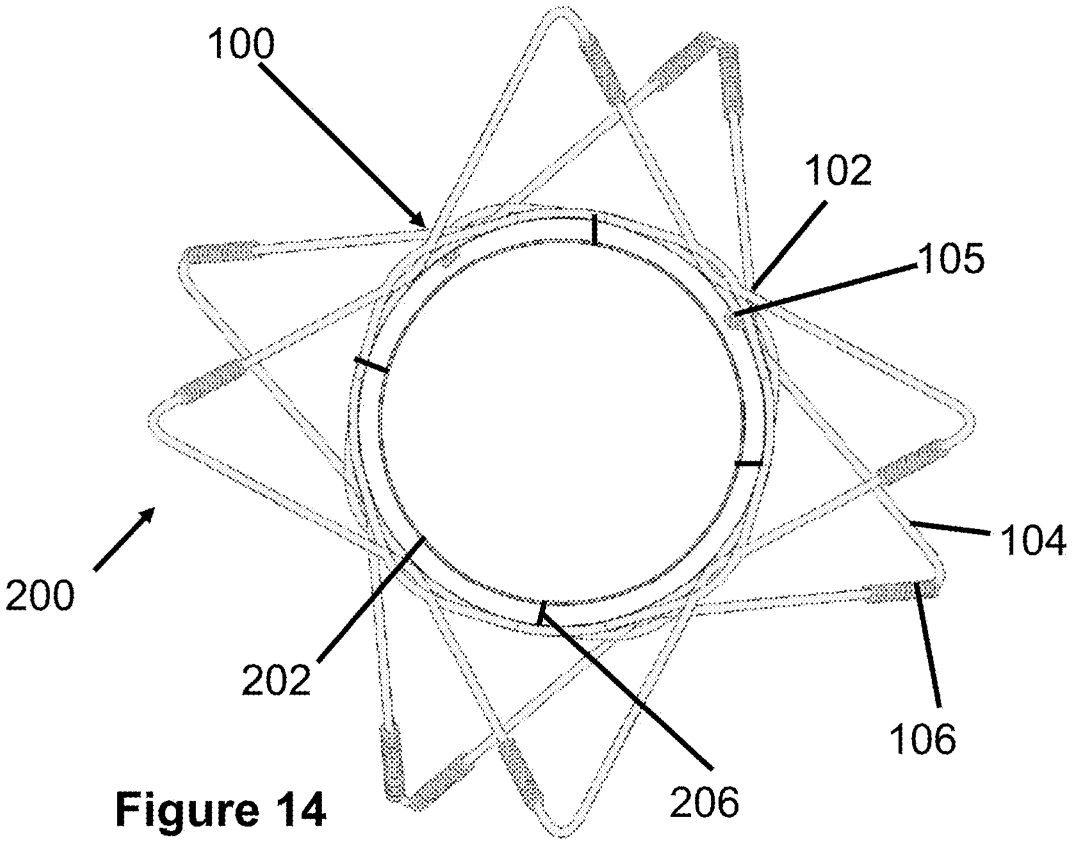

As best seen in FIGS. 13 and 14, the proximal end of the dual layer stent 200 includes a plurality of attachment members 206 that connect the anchoring stent 100 with the flow-diverting layer 202. The attachment members 206 can be composed of tantanlum wire (in this case is 0.001" dia.) and can be attached to portions of wire 102 and wire 202. In another embodiment, the proximal end of the flow-diverting layer 202 can be crimped on to the wires 102 of the anchoring stent 100. In another embodiment, portions of the stent 100 and flow-diverting layer can be woven through each other for attachment purposes. In yet another embodiment, the stent 100 can be formed with eye-loops (e.g., formed via laser cutting or etching) or similar features sized to allow wires 202 to be woven through for attachment purposes.

Since the anchoring stent 100 and the flow-diverting layer 202 may have different weave patterns or weave densities, both will shorten in length at different rates as their diameter expands. In this respect, the attachment members 206 are preferably located at or near the proximal end of the anchoring stent 100 and the flow-diverting layer 202 as oriented in the delivery device (i.e., on the end opposite the distal tip member 144). Hence, as the stent 200 is deployed, both the anchoring stent 100 and the flow-diverting layer 202 can decrease in length (or increase if retracting the stent 200 back into a delivery device), yet remain attached to each other. Alternately, attachment members 206 can be positioned at one or more locations along the length of the dual layer stent 200 (e.g., at the distal end, both ends, the middle, or at both ends and the middle region).

In one example embodiment of the stent 200, a flow-diverting layer 202 comprises 48 wires with a density of about 145 ppi and fully expands to a diameter of about 3.9 mm. An outer stent 100 comprises a single wire wound in a 2.5 revolution winding pattern and fully expands to a diameter of about 4.5 mm. When both layers 100 and 202 are fully expanded, the lengths are about 17 mm and 13 mm respectively. When both layers 100 and 202 are compressed on a 0.027 inch region of a delivery device, their lengths are about 44 mm and 37 mm respectively. When both layers 100 and 202 are expanded within a 3.75 mm vessel, their lengths are about 33 mm and 21 mm respectively.

In one preferred embodiment of the dual layer stent 200, the flow-diverting layer 202 is composed of wires 204 having a diameter between about 0.0005 inch and about 0.0018 inch and the wires 102 of the stent 100 have a diameter between about 0.0018 inch and about 0.0050 inch. Therefore, the minimum preferred ratio between the diameter of the wire 102 and wire 204 is about 0.0018 to 0.0018 inch respectively (or about a 1:1 ratio) and the maximum preferred ratio is about 0.0050/0.0005 inch (or about a 10:1).

It should be noted that the dual layer stent 200 can produce a larger amount of radial force (defined as the radial force exerted at about 50% radial compression of a stent) than either the stent 100 or flow diverting layer 200 alone. This higher radial force allows the dual layer stent 200 to have improved deployment and anchoring characteristics. In one example test of a dual layer stent embodiment, the outer stent 100 alone had an average radial force of about 0.13 N, the flow diverting layer 202 alone had an average radial force of about 0.05 N and the dual layer stent 200 had an average radial force of about 0.26 N. In other words, the average radial force of the stent 200 was greater than or equal to that of the flow diverting layer 202 and the stent 100 combined.

It should be noted that the porosity (i.e., the percentage of open space to non-open space) in the flow-diverting layer 202 changes as it radially expands. In this respect, a desired porosity or pore size can be controlled by selecting different sized stents 200 (i.e., stents that fully expand to different diameters). Table 1 below illustrates different example porosities that the flow-diverting layer 202 can achieve by varying the size of the stent 200 (i.e., its fully expanded diameter) in a particular target vessel. It should be understood that modifying other aspects of the flow-diverting layer 202, such as the number of wires used, picks per inch (PPI), or wire size may also modify porosity. Preferably, the flow-diverting layer 202 has a porosity between about 45-70% when expanded.

Similar techniques are also possible with regard to the porosity of the stent 100. Preferably, the stent 100 has a porosity when expanded that is between about 75% and 95% and more preferably a range between about 80% and 88%. Put a different way, the stent 100 preferably has a metal surface area or percentage of metal between about 5% and 25% and more preferably between 12% and 20%.

TABLE 1

| No. of Wires | PPI | Fully Expanded Stent OD (mm) | Expansion Size in Target Vessel (mm) | Porosity of Flow-Diverting Layer 202 |
|---|---|---|---|---|
| 48 | 145 | 2.9 mm | Fully Expanded | 50% |
| 48 | 145 | 2.9 mm | 2.75 mm | 56% |
| 48 | 145 | 2.9 mm | 2.50 mm | 61% |
| 48 | 145 | 3.4 mm | Fully Expanded | 51% |
| 48 | 145 | 3.4 mm | 3.25 mm | 59% |
| 48 | 145 | 3.4 mm | 3.00 mm | 64% |

TABLE 1-continued

| No. of Wires | PPI | Fully Expanded Stent OD (mm) | Expansion Size in Target Vessel (mm) | Porosity of Flow-Diverting Layer 202 |
|---|---|---|---|---|
| 48 | 145 | 3.9 mm | Fully Expanded | 52% |
| 48 | 145 | 3.9 mm | 3.75 mm | 61% |
| 48 | 145 | 3.9 mm | 3.50 mm | 67% |

The stent 100 can be "oversized" or have a larger internal diameter relative to the outer diameter of the flow-diverting layer 202 when in a fully expanded position or a target vessel (having a target diameter). Preferably, the difference between the inner surface of the stent 100 and the outer surface of the flow-diverting layer 202 is between about 0.1 mm and about 0.6 mm (e.g., a gap between about 0.05 mm and about 0.3 mm between the two). Generally, the dual layer stent 200 can be slightly oversized for a patient's target vessel. In this respect, the outer stent 100 can slightly push into the tissue of the target vessel, allowing the "undersized" flow-diverting layer 202 to maintain a profile that is relatively close to or even touching the tissue of the vessel. This sizing can allow the stent 100 to better anchor within the vessel and closer contact between the flow-diverting layer 202 and vessel tissue. It should be further noted that this "oversizing" of the dual layer stent 200 can result in about a 10-15% increase in the porosity of the flow-diverting layer 202 relative to the fully expanded (and unobstructed) position of the flow-diverting layer 202, as seen in the example data in Table 1.

The dual layer stent 200 can provide improved tracking and deployment performance, especially when compared to a stent of similar size and thickness to the flow-diverting layer 202. For example, tests have shown that a reduced amount of force is needed during deployment or retraction of the dual layer stent 200 from the delivery device in comparison to a stent similar to the flow-diverting layer alone. The inclusion of the outer stent 100 as part of the dual layer stent 200 reduces friction in the delivery system relative to the radial force and porosity of the stent 200.

Figure 19:
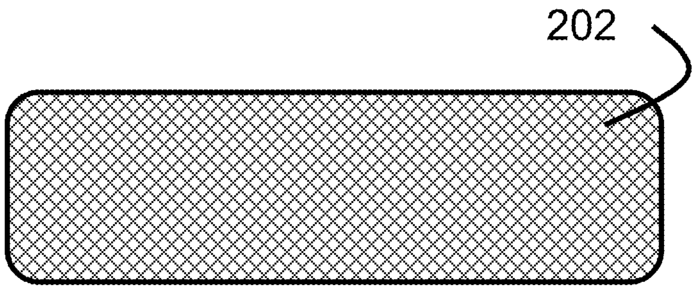
FIG. 19 illustrates a stent according to the present invention composed of a flow-diverting layer.

Preferably, the dual layer stent 200 can be deployed or retracted with between about 0.2 lbs and about 0.6 lbs of force. By including the stent 100 on the outside of the flow diverting layer 202, the deployment force can be reduced between about 10-50% as compared with the deploying/retracting the flow diverting layer 202 alone (i.e., a stand-alone layer 202 used by itself as seen in FIG. 19). Since less deployment force is required for the dual layer stent 200 as compared with a bare flow diverting layer 202, more desirable delivery characteristics can be achieved from a deployment device.

Figure 15:
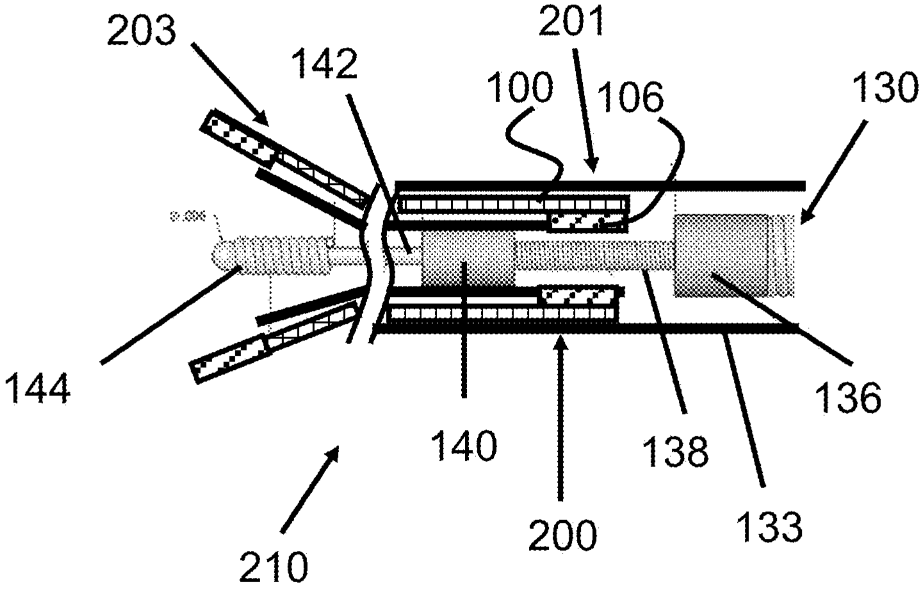
FIG. 15 illustrates a cross sectional view of a delivery system for the dual layer stent of FIGS. 12-14.

One example deployment and retraction force test was performed on an example dual layer stent 200 as seen in FIGS. 12-14 and a flow-diverting layer 202 alone, as shown in FIG. 19. The dual layer stent 200 required an average maximum deployment force of about 0.3 lbs and an average maximum retraction force of about 0.4 lbs. The stent of only a flow-diverting layer 202 had an average deployment force of about 0.7 lbs. Note that retraction of the flow-diverting layer 202 stent was not possible in the tests due to a lack of a locking or release mechanism (e.g., no coils 106 to contact marker band 140, as seen in FIG. 15). Preferably, the dual layer stent 200 includes differences in the diameter of the wire 102 of the outer stent 100, similar to those described for the embodiment of FIGS. 1-10. Specifically, the wire 102 making up the middle region of the stent 100 have a reduced diameter while the wire 102 at the ends (e.g., at loops 104) have a larger diameter than the middle region. For example, the middle region can be electropolished to reduce the diameter of wire 102 while the ends of the stent 100 can be protected from electropolishing, maintaining their original diameter. Put another way, the thickness of the stent 100 is thinner at a middle region. Note that this reduced thickness in the middle region is also applicable to embodiments of the outer stent that do not use wire (e.g., laser cut tube stent seen in FIG. 16). In test trials of an example embodiment of the dual layer stent 200 with this diameter difference, relatively low deployment and retraction forces were demonstrated. These lower deployment and retraction forces can provide desirable tracking, deployment and retraction characteristics. Preferably, the wires 102 of the middle region are between about 0.0003 inch and about 0.001 inch smaller in diameter or thickness than the distal and/or proximal regions of the stent 100. Preferably, the wires 102 of the middle region are between about 10% to about 40% smaller in diameter or thickness than the distal and/or proximal regions of the stent 100 and most preferably about 25% smaller.

For example, one embodiment included ends composed of wire 102 having a diameter of about 0.0025 inch and a middle region composed of wire 102 having a diameter of about 0.0021 inch. This embodiment averaged a maximum average deployment force of about 0.3 lbs within a range of about 0.2-0.4 lbs and a maximum average retraction force of about 0.4 lbs within a range of about 0.3-0.4 lbs.

Another embodiment included ends composed of wire 102 having a diameter of about 0.0020 inch and a middle region composed of wire 102 having a diameter of about 0.0028 inch. This embodiment averaged a maximum average deployment force of about 0.2 lbs within a range of about 0.2-0.3 lbs and a maximum average retraction force of about 0.3 lbs in a range of about 0.3-0.4 lbs.

Another embodiment included ends composed of wire 102 having a diameter of about 0.0021 inch and a middle region composed of wire 102 having a diameter of about 0.0028 inch. This embodiment averaged a maximum average deployment force of about 0.4 lbs within a range of about 0.3-0.4 lbs and a maximum average retraction force of about 0.6 lbs in a range of about 0.5-0.6 inch.

Turning to FIG. 15, a delivery device 210 is shown according to the present invention for deploying the stent 200 within a patient. The delivery device 210 is generally similar to the previously described delivery device 135, including a sheath 133 disposed over a delivery pusher 130 to maintain the stent 200 in a compressed position over marker band 140.

As with the previous device, a proximal end 201 of the stent 200 is disposed over distal marker band 140 and proximal coil members 106 are positioned between marker bands 136 and 140. The stent 200 can be deployed by proximally retracting the sheath 201 relative to the pusher 130. The stent 200 can also be retracted (if it was not fully deployed/released) by retracting the pusher 130 in a proximal direction, thereby causing the marker band 140 to contact the proximal coil members 106, pulling the stent 200 back into the sheath 133.

As previously described, the proximal end 201 of the stent 200 includes attachment members 206 (not shown in FIG. 15) which connect the stent 100 with the flow-diverting layer 202. In this respect, as the sheath 133 is proximally retracted during deployment and a distal portion 203 of the dual layer stent 200 begins to radially expand, the stent 100 and the flow-diverting layer 202 can decrease in length at different rates.

A portion of the wire 105 can be woven along the length of the stent 100 in a distinctive pattern. This length can correspond to the length and position of the inner flow diverting layer 202, thereby indicating the length and position of the inner flow diverting layer 202 to the user during a procedure.

In another preferred embodiment according to the present invention, the flow-diverting layer 202 may be woven into the anchoring stent 100.

Figure 16:
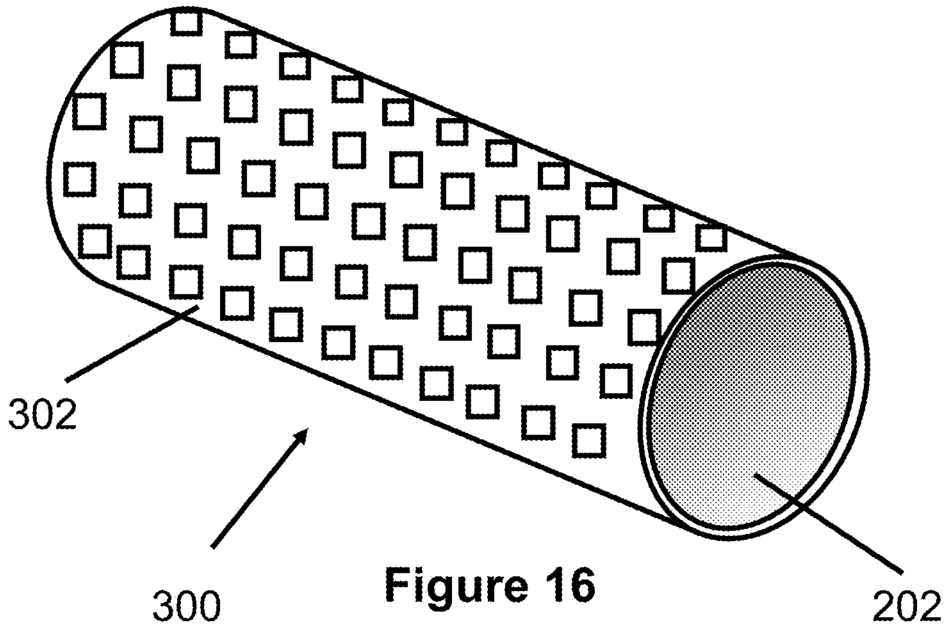
FIG. 16 illustrates a perspective view of dual layer stent having an outer stent layer formed from a tube or sheet of material.
Figure 17:
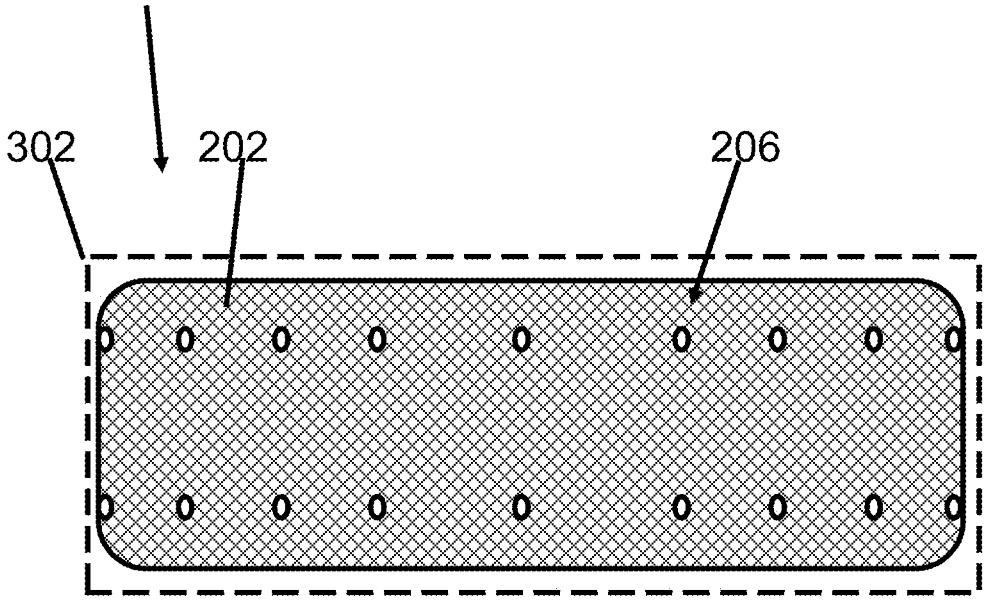
FIG. 17 illustrates a cross sectional view of the dual layer stent of FIG. 15 showing various optional attachment points of both layers of the dual layer stent.

FIG. 16 illustrates another embodiment according to the present invention of a dual layer stent 300 comprising an inner flow-diverting layer 202 and an outer stent 302. Preferably, the outer stent 302 is formed by cutting a pattern (e.g., laser cutting or etching) in a sheet or tube composed of a shape memory material (e.g. Nitinol). FIG. 16 illustrates a pattern of a plurality of diamonds along the length of the outer stent 302. However, it should be understood that any cut pattern is possible, such as a plurality of connected bands, zig-zag patterns, or wave patterns.

The cross sectional view of the dual layer stent 300 illustrates a plurality of example positions for attachment member 206 to connect the outer stent 302 and inner flow-diverting layer 202. As with any of the previously described embodiments, the attachment members 206 (or other methods of attachment such as welding or adhesive) can be located at one or more of the example locations shown. For example, attachment members 206 may be located at the proximal end, distal end, or the middle. In another example, attachment members 206 can be located at both the proximal and distal ends. Alternately, no attachment members 206 or attachment mechanism are used to attach the inner flow-diverting layer 202 with the outer stent 302.

Figure 18:
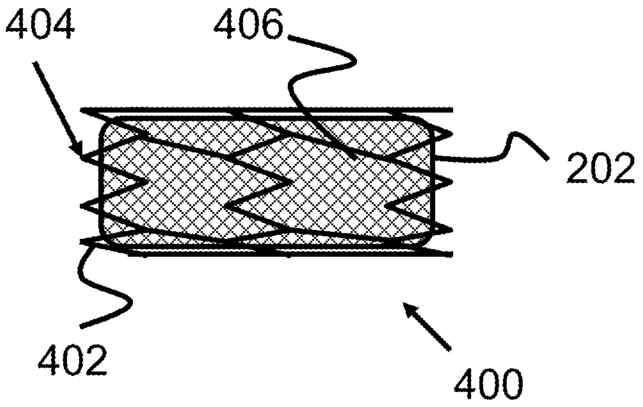
FIG. 18 illustrates another preferred embodiment of a dual layer stent according to the present invention.

FIG. 18 illustrates another embodiment of a dual layer stent 400 according to the present invention. The stent 400 comprises an inner flow-diverting layer 202 attached to an outer stent 402. The outer stent 402 comprises a plurality of radial, zigzag bands 404 that are bridged or connected via longitudinal members 406. Preferably, the stent 402 can be created by welding a plurality of members together, laser cutting or etching this pattern into a sheet or tube, or using vapor deposition techniques. As with previous embodiments, the flow-diverting layer 202 can be attached to the outer stent 402 near the distal end, proximal end, middle region, or any combination of these locations.

Figure 20:
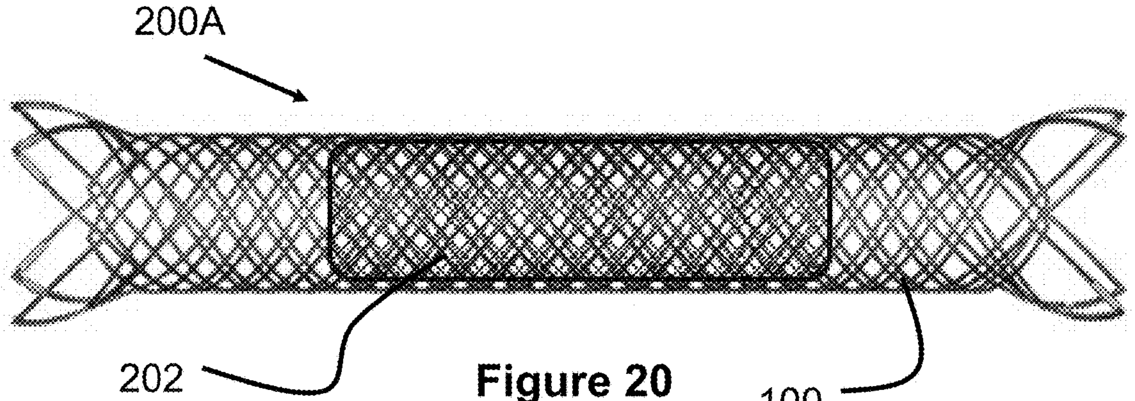
FIG. 20 illustrates a dual layer stent according to the present invention having a shortened flow-diverting layer.

As best seen in FIGS. 12 and 13, the flow-diverting layer 202 preferably has a length that extends near the ends of the main body portion of stent 100 and stops near the formation of the loops 104. However, the flow-diverting layer 202 can alternately include any range of lengths and positions relative to the stent 100. For example, FIG. 20 illustrates a dual layer stent 200A in which the flow-diverting layer 202 is shorter in length than the stent 100 and longitudinally centered or symmetrically positioned.

Figure 21:
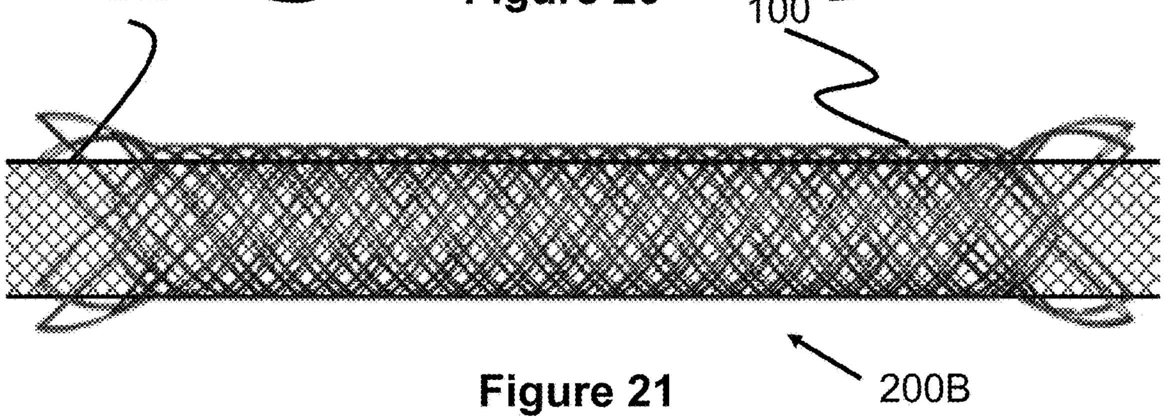
FIG. 21 illustrates a dual layer stent according to the present invention having an elongated flow-diverting layer.

In another example, FIG. 21 illustrates a dual layer stent 200B in which the flow-diverting layer 202 is longer in length than the stent 100. While the flow-diverting layer 202 is shown as being longitudinally centered within the stent 100, asymmetrical positioning of the flow-diverting layer 202 is also contemplated.

Figure 22:
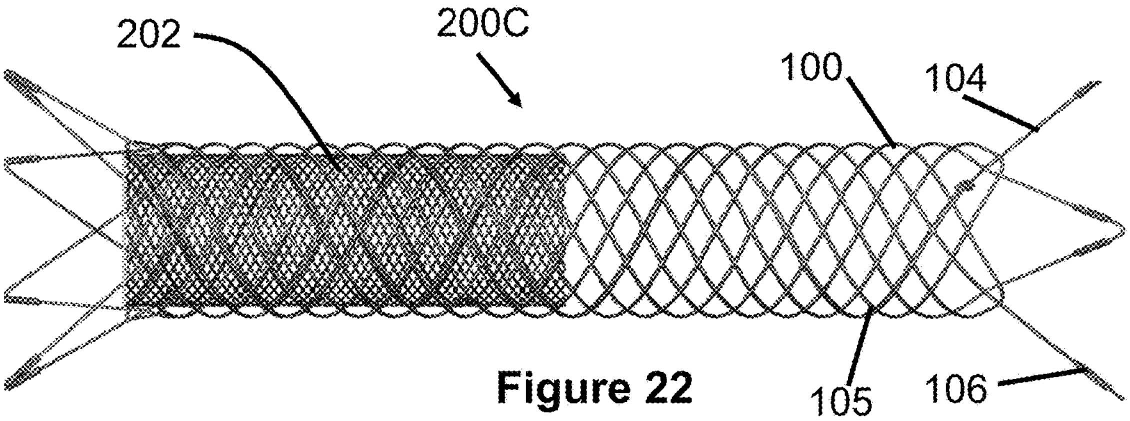
FIG. 22 illustrates a dual layer stent according to the present invention having an asymmetrically positioned flow-diverting layer.

In yet another example, FIG. 22 illustrates a dual layer stent 200C in which a flow-diverting layer 202 is shorter in length than the stent 100 and asymmetrically positioned within the stent 100. In this example, the flow-diverting layer 202 is positioned along the proximal half of the stent 100, however, the flow-diverting layer 202 may also be positioned along the distal half of the stent 100. While the flow-diverting layer 202 is shown extending about one half of the length of the stent 100, the flow-diverting layer 202 may also span one third, one quarter or any fractional portion of the stent 100.

Figure 23:
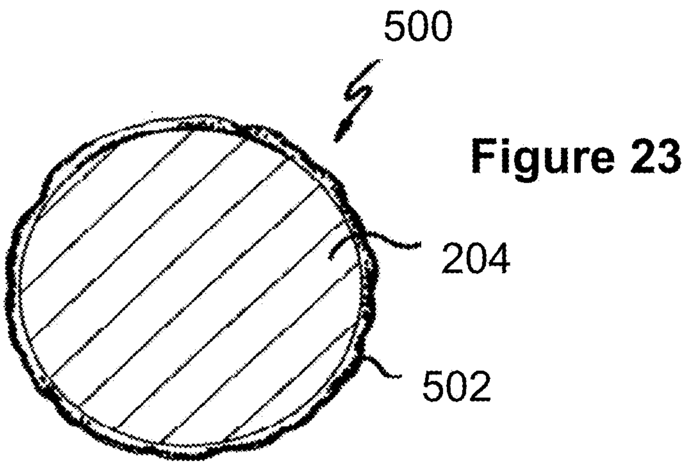
FIGS. 23 and 24 illustrate an expansile wire for use with a flow-diverting layer according to the present invention.
Figure 24:
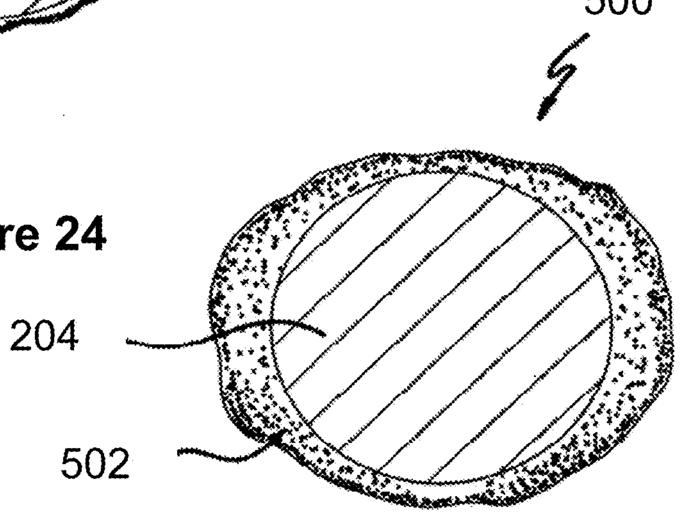
Figure 25:
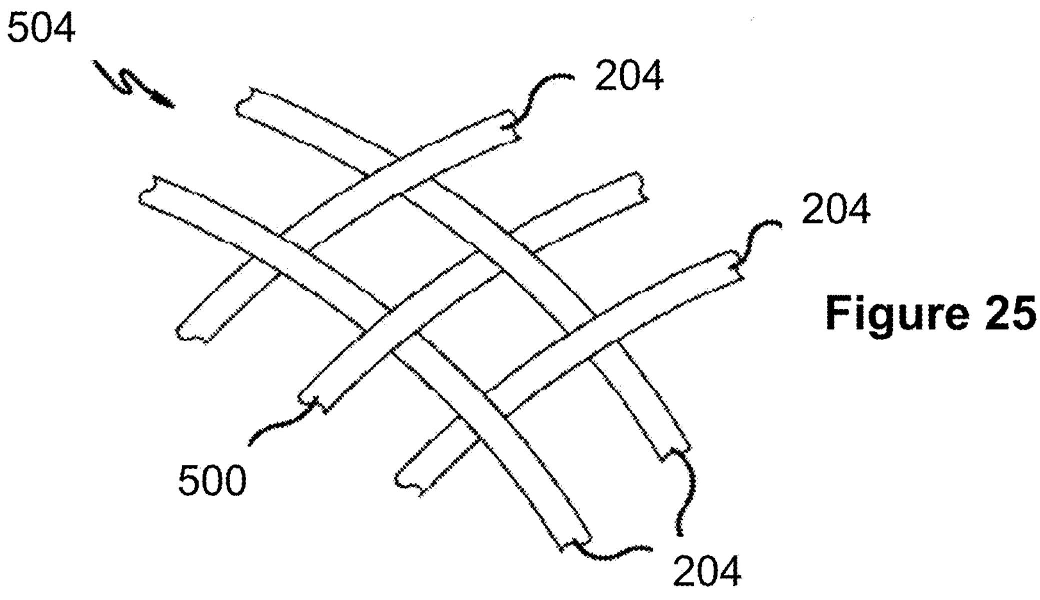
FIG. 25 illustrates a portion of a flow-diverting layer having an expansile wire incorporated into its structure.
Figure 26:
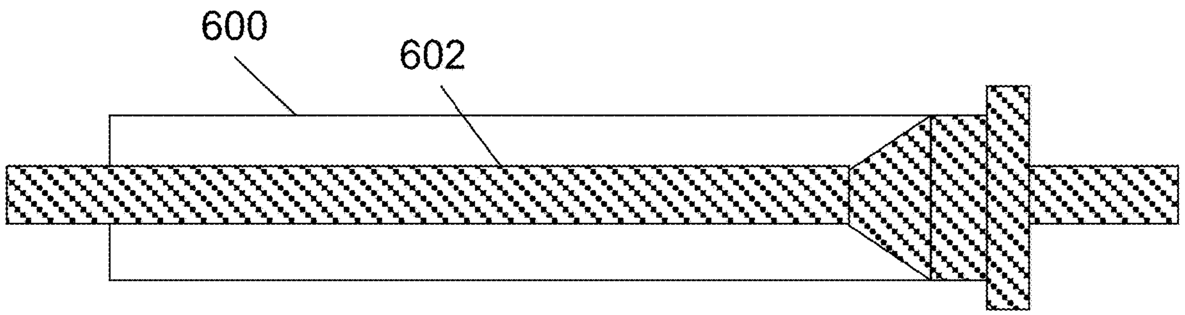
FIG. 26-29 illustrate a process according to the present invention for creating a polymer stent or stent layer.

Turning to FIGS. 23-25, the flow-diverting layer 202 can be composed of one or more expansile wires 500 or filaments. Preferably, the expansile wires 500 are composed of the previously described wires 204 that are coated with a hydrogel coating 502 that expands in a patient's vessel. The wires 204 may be composed of a shape memory metal (e.g., nitinol), a shape memory polymer, nylon, PET or even entirely of hydrogel. As seen in FIG. 25, the hydrogel wires 500 can be woven amongst wires 204 which are not coated with hydrogel. Alternately, partial lengths of the wires can be coated with hydrogel so as to coat only a specific region of the flow-diverting layer 202 (e.g., the center region).

In any of the previous embodiments, one or more of the stent layers (e.g., stent 100 or flow diverting layer 202) can be mostly composed of a polymer (e.g., a hydrogel, PET (Dacron), nylon, polyurethane, Teflon, and PGA/PGLA). Generally, a polymer stent can be manufactured by the free radical polymerization of a liquid prepolymer solution within a container of a desired shape.

One example polymer stent manufacturing technique can be seen in FIGS. 26-29. Starting with FIG. 26, a generally cylindrical mandrel 602 is placed within a tube 600. Preferably, the mandrel 602 can create a fluid-tight seal on at least one end of the tube 600 and preferably the opposing end of the tube 600 is also closed.

Figure 27:
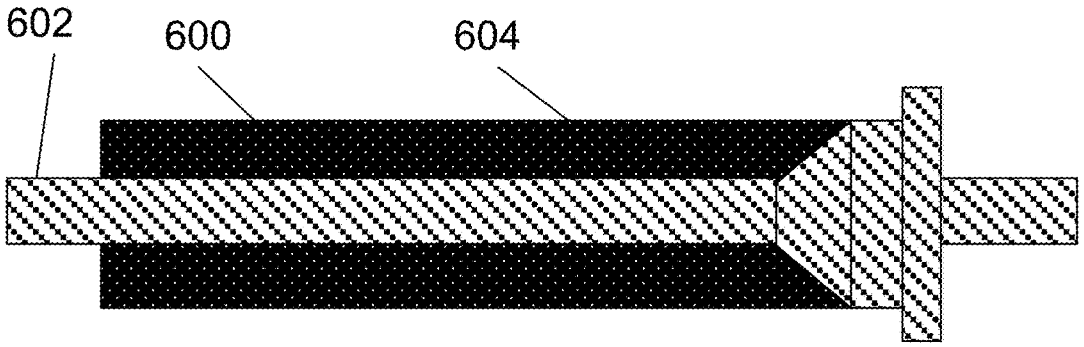
Figure 28:

In FIG. 27, a liquid prepolymer is injected into the space between the mandrel 602 and the tube 600. Polymerization is induced in the prepolymer solution (e.g., heating at 40-80° C. for 12 hours). Once polymerized, the tube 600 and mandrel 602 are removed from the solid polymer tube 606, shown in FIG. 28. This tube 606 can be washed to eliminate residual monomers and dried over a mandrel to maintain shape.

Figure 29:
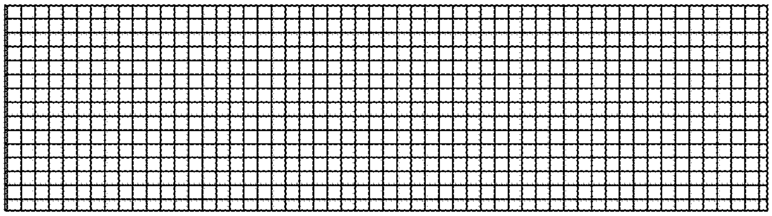

Finally, the polymer tube 606 can be laser cut, CNC machined, etched or otherwise shaped into a desired pattern, as seen in FIG. 29. The length and thickness of the final stent can also be modified during the manufacturing process by changing the diameter or length of the tube 606 or the mandrel 602.

Figure 30:
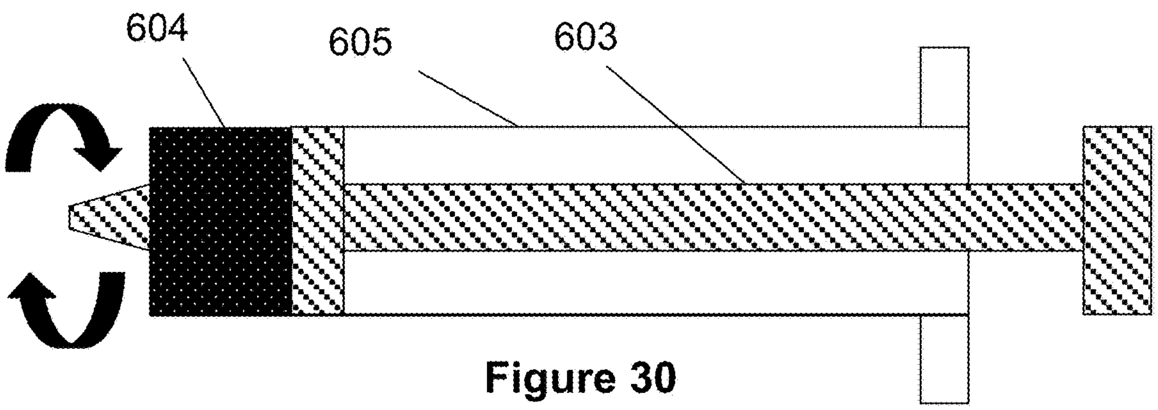
FIG. 30 illustrates another process according to the present invention for creating a polymer stent or stent layer.

In another example stent manufacturing process seen in FIG. 30, centrifugal force is used to disperse the prepolymer solution along the inside of a syringe tube 605. Specifically, a plunger 603 is positioned in the tube 605 and a predetermined amount of prepolymer solution 604 is taken into the syringe tube 605. The syringe tube 605 is connected to a mechanism that causes the tube 605 to spin in a horizontal orientation along a longitudinal axis of the tube 605 (e.g., an overhead stirrer positioned horizontally with its rotating member connected to the tube 605).

Once the tube 605 achieves a sufficient rotational speed (e.g., about 1500 rpm), the syringe plunger 603 is pulled toward the end of the tube 605, taking in a gas such as air. Since the prepolymer solution now has more space to spread out, the centrifugal force causes an even coating to form on the wall of the tube 605. Polymerization can be initialed using a heat source (e.g., a heat gun) and then heated (e.g., 40-80° C. for 12 hours). The solid polymer tube can then be removed from the tube 605, washed to eliminate residual monomers, dried on a mandrel, and then laser cut, CNC machined, etched or otherwise shaped into a desired pattern.

Figure 31:
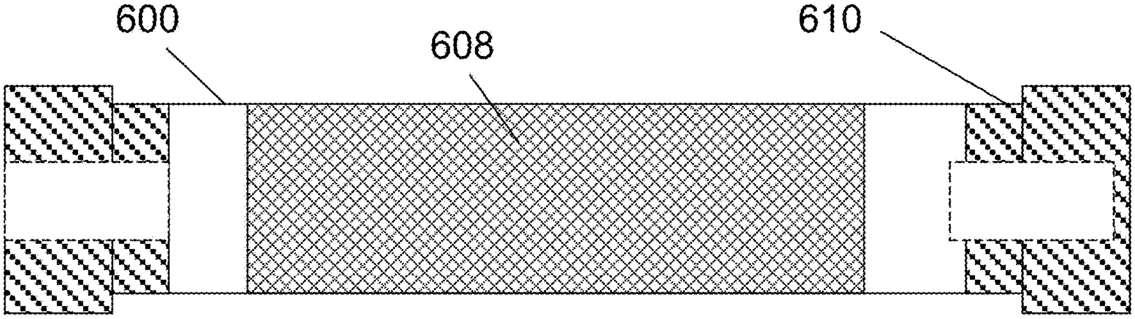
FIGS. 31-36 illustrate another process according to the present invention for creating a polymer stent or stent layer.

FIGS. 31-36 illustrate yet another example process for creating a polymer stent according to the present invention. Turning first to FIG. 31, a plastic or degradable rod 608 is placed in tube 600 and luer adapters 610 are connected to each opening of the tube 600. The rod 608 has an engraved or depressed pattern (e.g., created by laser machining, CNC machining or other suitable method) on its outer surface in the patter desired for the final stent. When the rod 608 is placed in the tube 600, these patterns form channels that are later filled by the prepolymer 604. In other words, the outer diameter of the rod 608 and the inner diameter of the tube 600 are such that the prepolymer 604 is prevented from moving outside the channels or patterned area.

Figure 32:
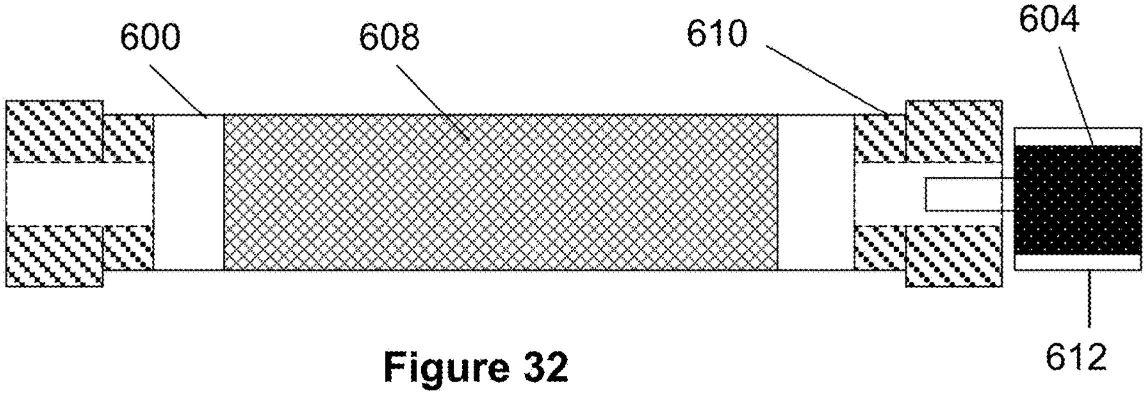
Figure 33:
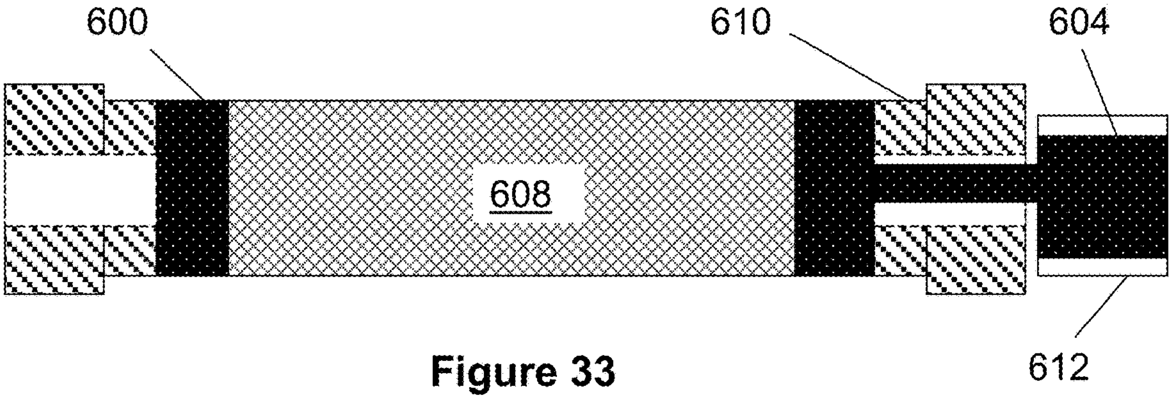

As seen FIG. 32, a syringe 612 is inserted into a luer adapter 610 and prepolymer solution 604 is injected into the tube 600 as seen in FIG. 33. The prepolymer solution 604 fills into the pattern on the surface of the rod 608. The syringe 612 is removed from the luer adapter 610 and polymerization is completed by heating the prepolymer solution 604 (e.g., 40-80° C. for about 12 hours).

Figure 34:
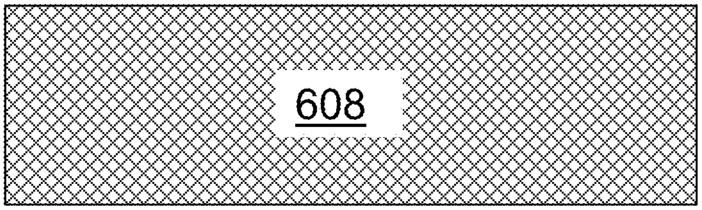
Figure 35:
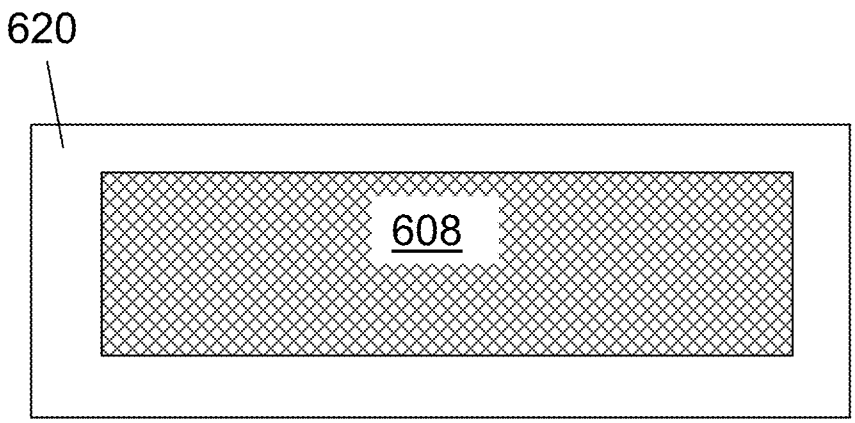
Figure 36:
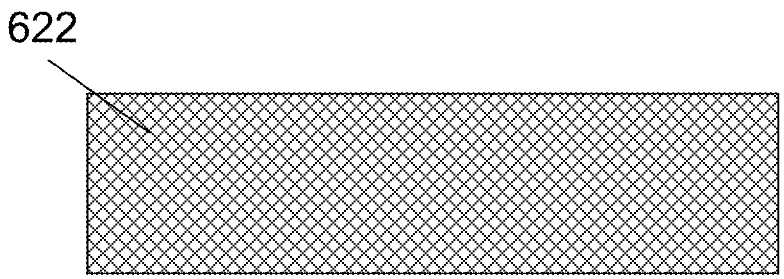

The rod 608 is removed from the tube 600 as seen in FIG. 34 and placed in an organic solvent bath 622 as seen in FIG. 35. The organic solvent bath 622 dissolves the rod 608, leaving only the polymer stent 622 (FIG. 36) having the same pattern as the surface of the rod 608.

It should be noted that different aspects of the stent 622 can be controlled by changing the pattern on the surface of the rod 608, the diameter of the rod 608 and the tube 600, the length of the rod 608 and tube 600 and similar dimensions. Additional modification is also possible by laser cutting, CNC machining, etching, or similar processes.

FIGS. 37-50 illustrate various modifications of delivery pusher 130 which have been previously described in this embodiment. Some of the embodiments include a friction region of larger diameter near a distal end of the pusher to prevent the stent from over compressing and creates friction between the stent and pusher to help push the stent out of the catheter sheath. Additionally, when the friction region is in contact with the inner surface of the stent, it allows the physician to pull the stent out of the delivery sheath rather than pushing on the stent from its proximal end. Hence, the stent may require less rigidity. Furthermore, the friction region distributes the deployment force from the pusher over a greater surface area of the stent, thereby reducing stress on the stent that can result from pushing or pulling on the stent at a single location. This distribution of force makes the delivery system more reliable since the strength of the bond between the delivery pusher and the friction region can be lower than would be otherwise required if the stent was pushed or pulled from a single location. Including the friction region with pushing or pulling features of the marker bands also creates a redundancy for both advancing the stent our of the catheter or retracting the stent back into the catheter, since if one mechanism fails, the other would allow the physician to complete the procedure.

Figure 37:
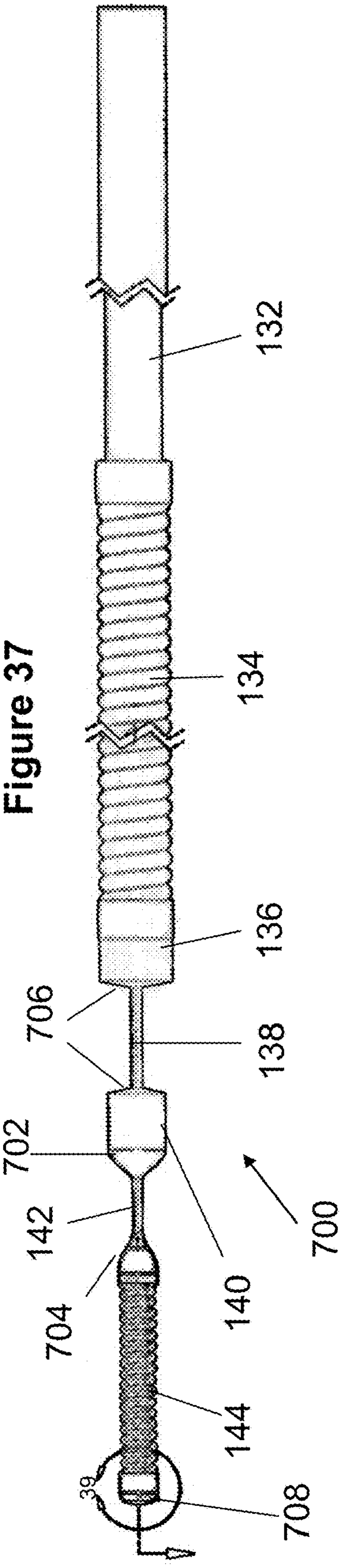
FIGS. 37-39 illustrate various aspects of a stent delivery pusher according to the present invention.
Figure 38:
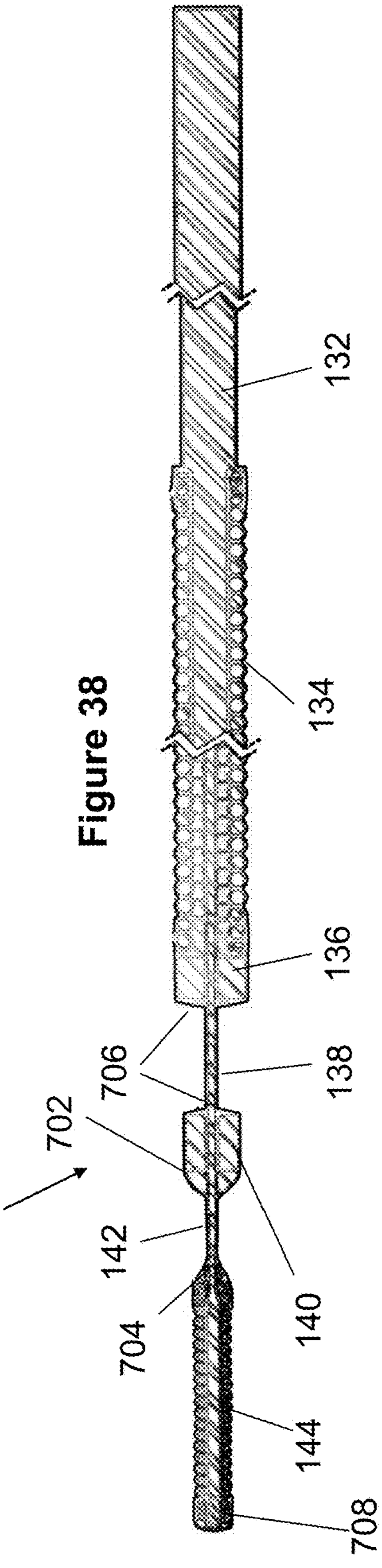
Figure 39:
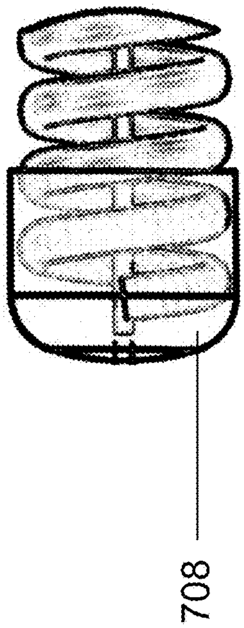

In FIGS. 37-39, the pusher 700 includes several tapered or conical regions between the marker bands 136 and 140. Specifically, the pusher 700 includes two regions of UV adhesive: a distal region 708 at the distal end of the coiled distal tip member 144 and a tapered or conical region 704 at the proximal end of the tip member 144. The second marker band 140 includes a distal tapered region 702 composed of epoxy (e.g., EPOTEK 353). The proximal face of marker band 140 and the distal face of marker band 136 include a small amount of epoxy 706 that is shaped to a slight taper or conical shape. The marker bands 136 and 140 and coiled tip member 144 are preferably composed of platinum. The core wire 132 is preferably composed of Nitinol and the coil 134 is preferably composed of stainless steel. In one example, the distance between markers 136 and 140 is about 0.065, the distance between marker 140 and conical region 704 is about 0.035 cm, and the coiled tip is about 0.100 cm in length.

Figure 40:
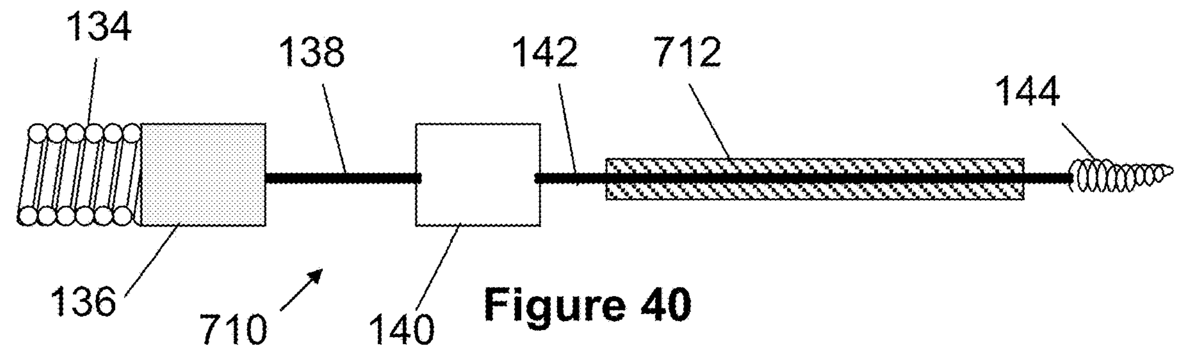
FIGS. 40-50 illustrates various embodiments of stent delivery pushers having different distal end shapes according to the present invention.

In the pusher embodiment 710 of FIG. 40, an elongated polymer region 712 (e.g., PET, Teflon, Pebax, nylon, PTFE) is located on section 142 of the core member 132 between the distal marker band 140 and the distal tip 144. This polymer region 712 can be formed from a shrink tube having a thickness of about 0.00025 inches or from braided polymer strands. One advantage of the polymer region is that it adds some thickness to the core wire and thereby prevents the stent (which is compressed on top) from over-compressing or collapsing when advanced through highly tortuous vessels of a patient.

Figure 41:
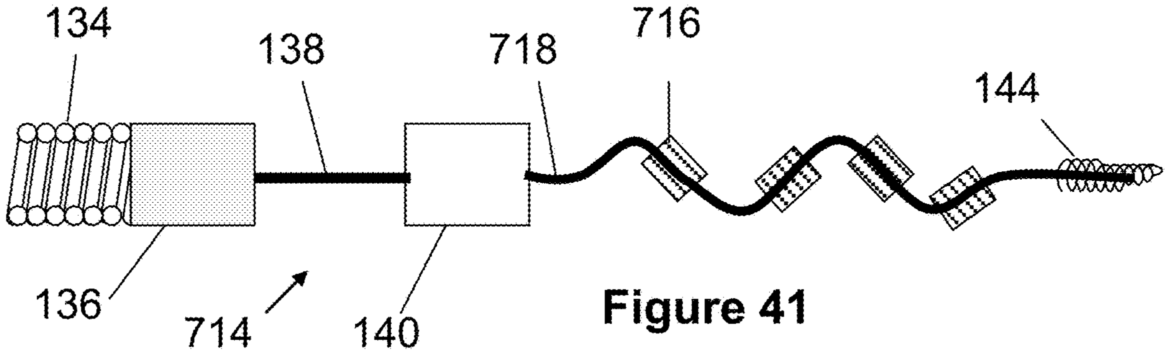

FIG. 41 illustrates a pusher embodiment 714 having a plurality of spaced apart sections 716 having a diameter that is larger than that of the core wire. These sections can be composed of polymer (e.g., shrink tube or braiding) or from a non-polymer material. A portion of the core wire 718 can be pre-shaped to have a plurality of curves or a wave shape. The wave region and material sections may prevent the stent from over-compressing during tortuous passage through a vessel. Additionally, the wave shapes may help force open a stent as it is delivered from the catheter. More specifically, the wave shape may be relatively straight when a stent is compressed over the wave shape in the delivery device, but expands as it exits the catheter, forcing the stent open. This stent expansion may be especially important when delivering the stent to a curved or bent vessel where the physician would typically push the delivery system forward to assist in causing the stent to open. In this respect, the delivery system would be less operator-dependent since the delivery system would pushed open automatically by the pusher 714. By including multiple material sections 716, the curves of the wave region may be better retained when expanded as compared to a single elongated polymer section (e.g., FIG. 41).

Figure 42:
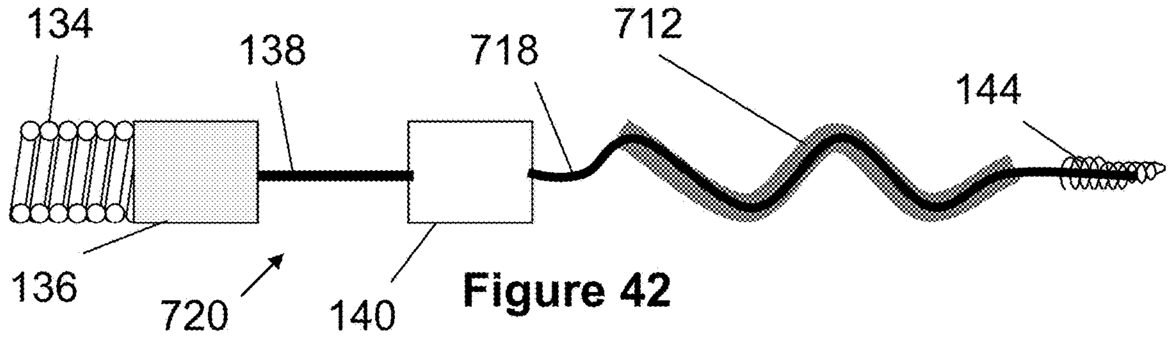
Figure 43:
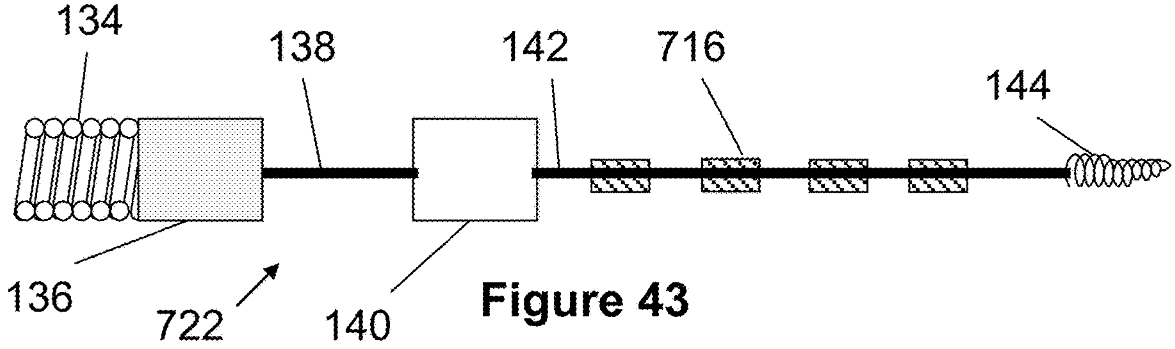

FIG. 42 illustrates a pusher embodiment 720 having an elongated polymer region 712 similar to the embodiment of FIG. 40 and a wave region 718 similar to the embodiment of FIG. 41. FIG. 43 illustrates a pusher embodiment 722 having multiple polymer areas 716 similar to the embodiment of FIG. 41 and a generally straight core wire 142 at the distal end of the pusher, similar to that of FIG. 40.

Figure 44:
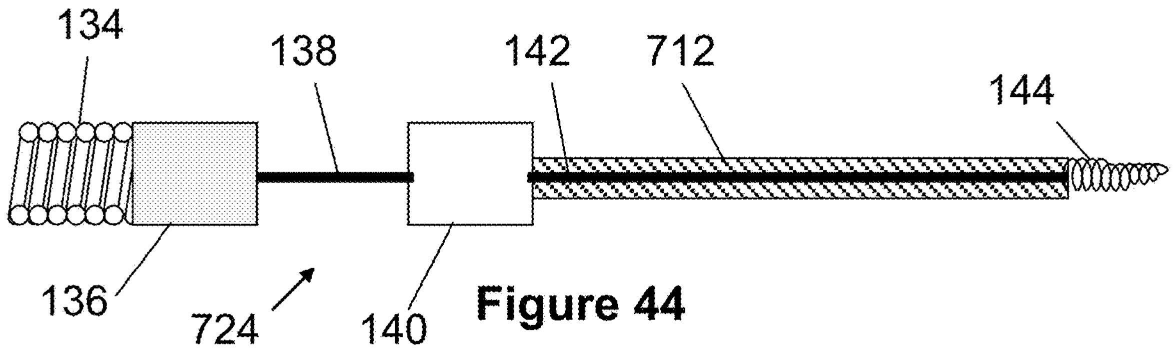

FIG. 44 illustrates a pusher embodiment 724 having an elongated straight region with a polymer region similar to the embodiment of FIG. 40. However, this polymer region extends the entire length between the distal marker band 140 and the distal tip 144.

Figure 45:
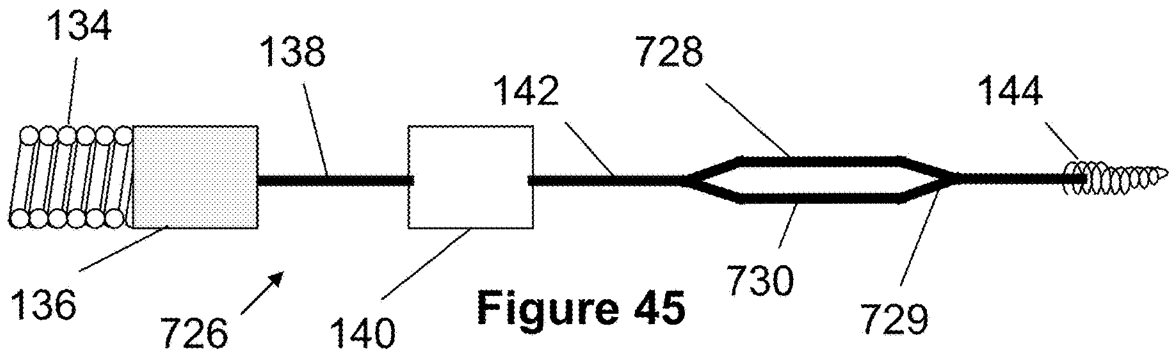

FIG. 45 illustrates a pusher embodiment 726 forming a closed loop between the distal marker band 140 and the distal tip 144 of the pusher 726 (i.e., an aperture in region 142 of the core member). This loop may prevent the stent from collapsing or over-compressing on the pusher, especially when advanced through tortuous vessels. Preferably, this loop is formed by welding both ends of a Nitinol wire 728 to an area 730 of the pusher's core wire. Both the attached wire 728 and the area of the core wire 730 can be bent or angled at each end to form an elongated loop shape of varying sizes. In this regard, the core member forms two opposing, branching shapes who's arms connect together to form an aperture or loop.

Figure 46A:
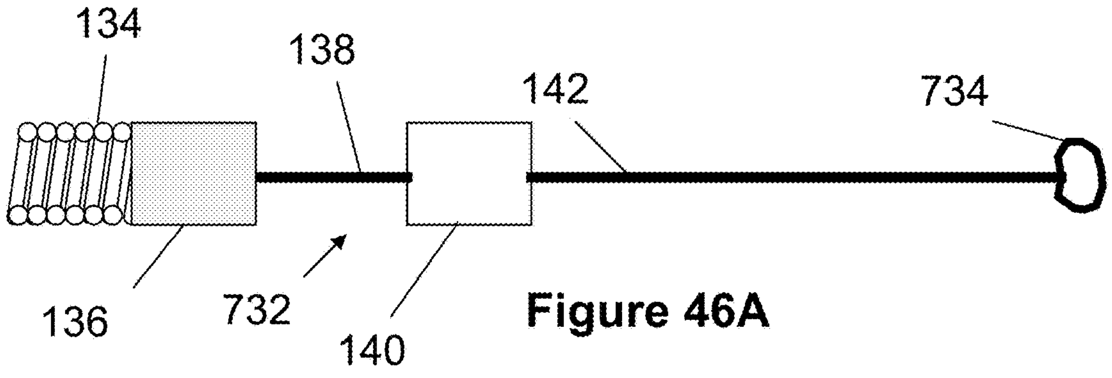
Figure 46B:
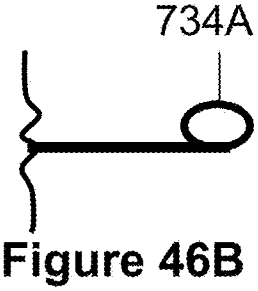
Figure 46C:
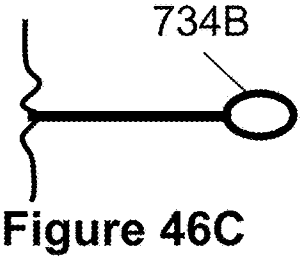

FIG. 46A illustrates a pusher embodiment 732 having a generally straight distal end 142 that terminates in a pigtail shape 734. The pigtail shape 734 can be created by bending the core wire 142 in several different orientations, as seen in FIG. 46A. For example, the pigtail shape 734B can be symmetrically positioned on the core wire (FIG. 46C) or asymmetrically offset 734A in one direction (FIG. 46B). This pigtailed shape helps to resist the stent from collapsing or over-compressing, thus aiding in the deployment and retrieval of the device.

Figure 47:
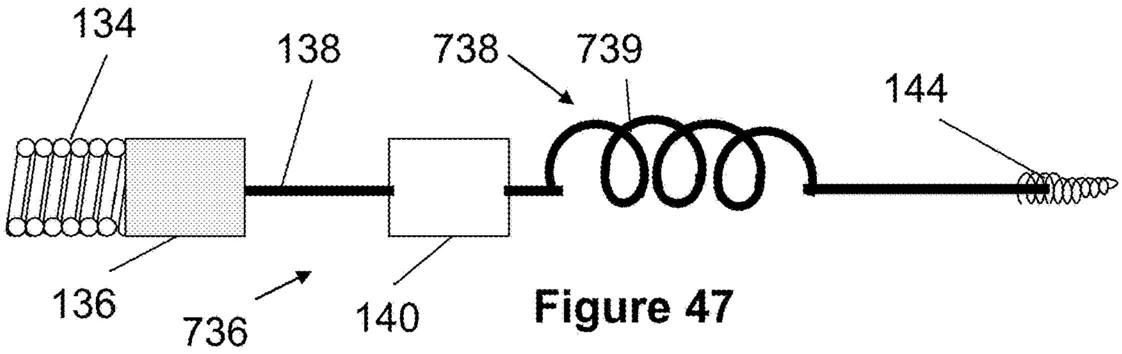
Figure 48:
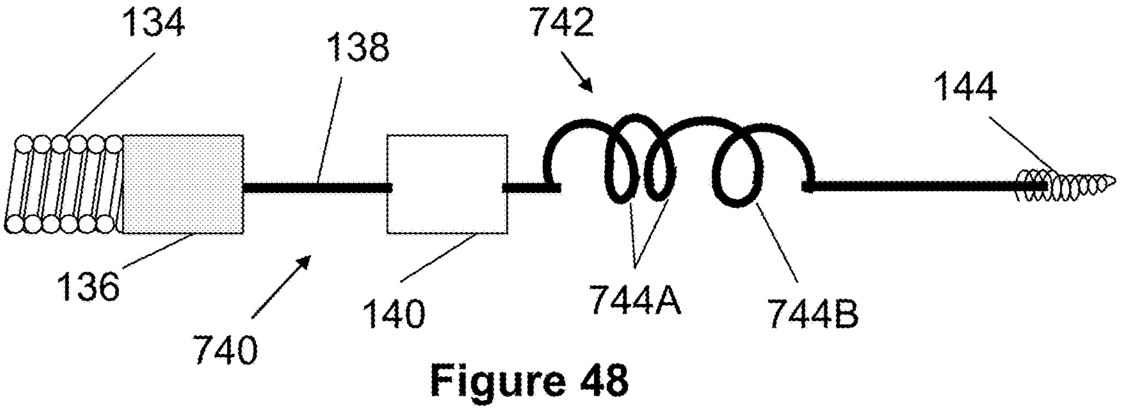
Figure 49:
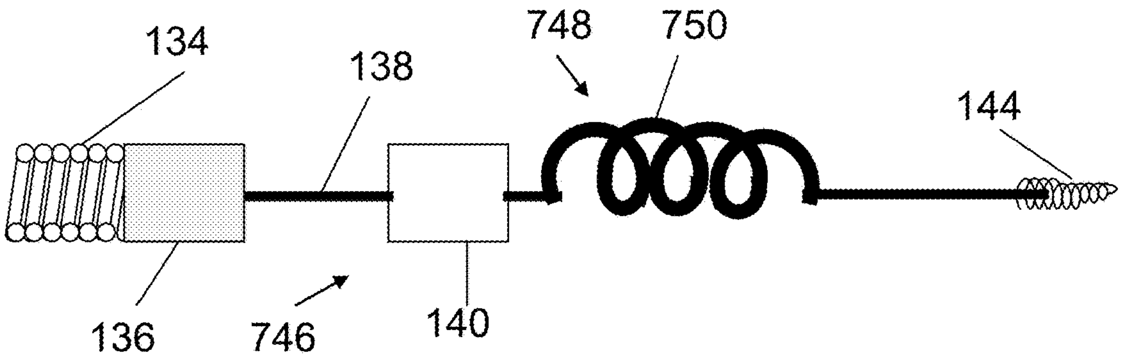
Figure 50:
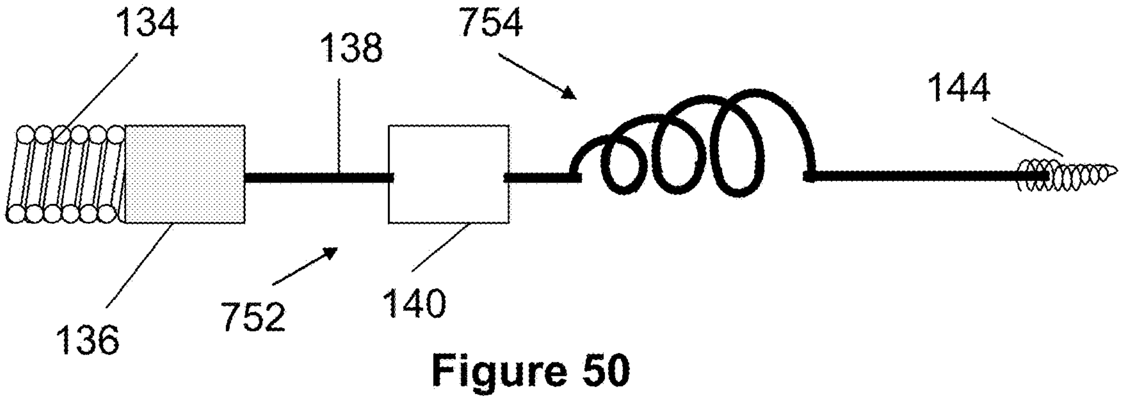

FIG. 47 illustrates a pusher 736 with a spiral or coil region 738 formed from a plurality of loops 739 near its distal end. The spiral region may encompass all exposed areas of the core wire or a fractional length. The pusher 740 of FIG. 48 illustrates a coil region 142 in which some loops 744A are relatively close together, while other loops 744B have a larger spacing from each other. Additionally, the spiral region 748 of pusher 746 in FIG. 49 may include a continuous or segmented coating or jacket 750 along its length or adjacent to the spiral region (e.g., PET, Teflon, Pebax, nylon, PTFE). Similar to previous embodiments, the spiral region increases the diameter of the pusher's distal end and thereby prevents the stent from collapsing or over compressing. However, since the spiral region's effective diameter increase of the pusher can be achieved without necessarily increasing the diameter of the core wire, flexibility of the pusher is generally similar to embodiments with straight distal core wires. The spiral region 754 of pusher 752 may also vary in diameter or pitch (e.g., increasing pitch, decreasing pitch, or discrete sections of different diameters) as seen in FIG. 50 and is preferably selected based on based on the shape, size and properties of the stent.

FIGS. 51-59 disclose an embodiment of a rapid exchange delivery device 770 for delivering a stent 793. While this delivery device 770 may be used for a variety of locations, it may be particularly useful for delivering stents in the carotid arteries for treatment of peripheral artery disease.

Figure 51:
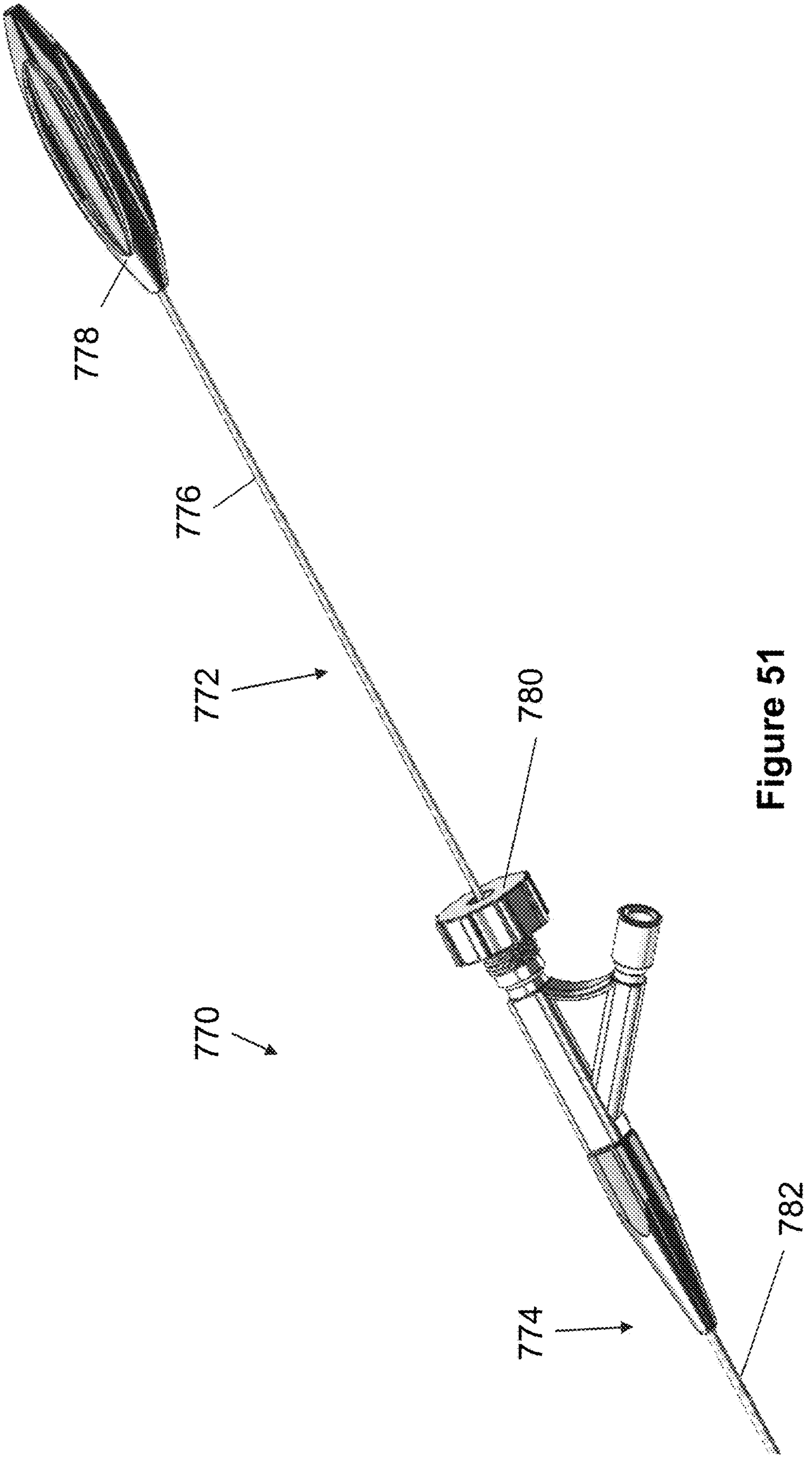
FIGS. 51-59 illustrate various embodiments of a rapid exchange stent delivery system according to the present invention.
Figure 52:
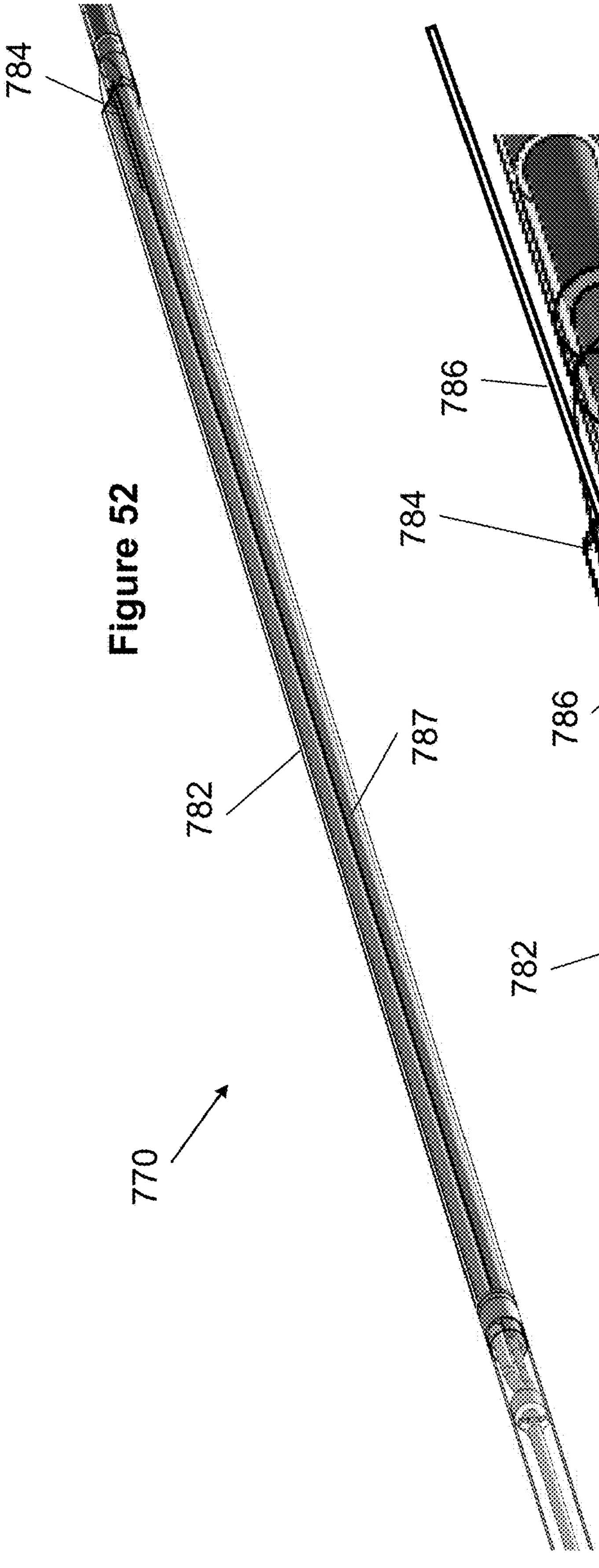

Turning first to FIG. 51, the device 770 includes a pusher member 772 having an elongated core member 776 that slides within a catheter 774, through proximal catheter port 780. Preferably, the proximal end of the core wire includes a handle 778 for facilitating movement of the pusher member 772 relative to the catheter 774.

Figure 53:
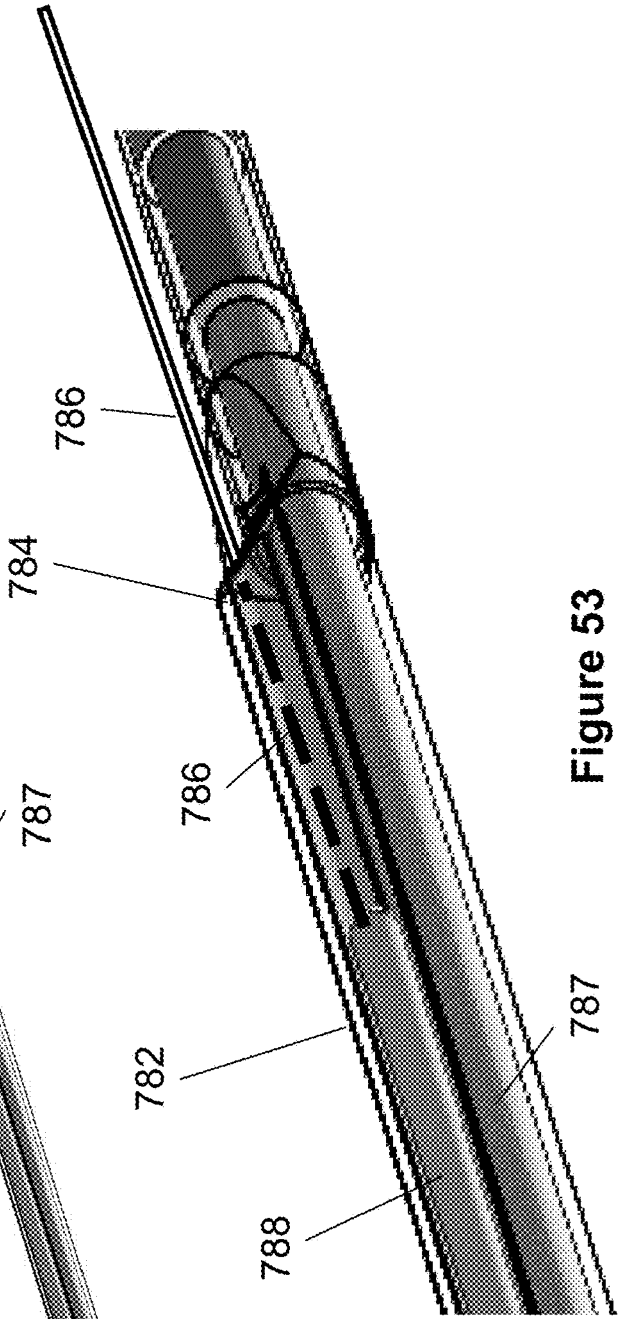
Figure 58:
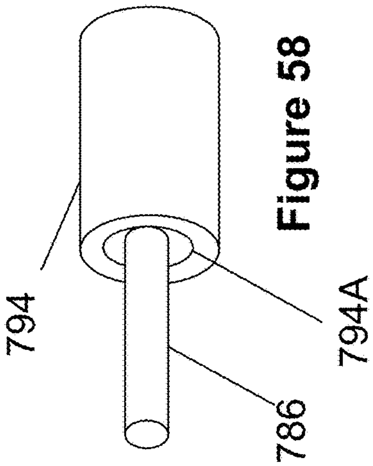
Figure 59:
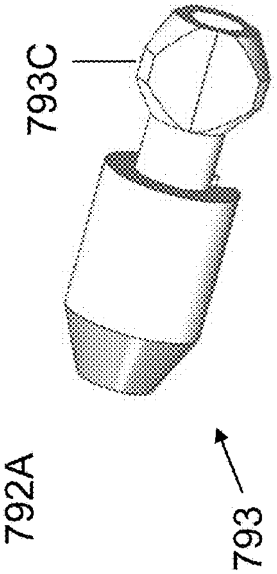

Instead of providing a guide wire passage that extends throughout the entire length of the catheter 774, the catheter 774 preferably includes a shortened "rapid exchange" passage in which the guide wire 786 only passes through a relatively short, distal portion of the catheter 774 (e.g., 5-10 inches). Once a distal end of the guide wire 786 is positioned near a target location, the proximal end of the guide wire 786 is inserted into a rapid exchange port 794A of a distal guide wire tube 794, as seen in FIG. 58. As seen best in FIGS. 55-57, the proximal end of the guide wire 786 passes through the distal guide wire tube 794 and into catheter tube 788. Finally, as best seen in FIG. 53, the guide wire 786 exits tube 788, passes through a remaining portion of the outer catheter tube 782, and exits the catheter at rapid exchange port 784.

Returning to FIGS. 55-57, the distal guide wire tube 794 extends into catheter tube 788 in a telescoping arrangement. Preferably, the distal guide wire tube 794 extend into the catheter tube 788 by at least the same distance the catheter 774 is retracted relative to the pusher 772. In this respect, the distal guide wire tube 794 and the catheter tube 788 maintain a continuous passage for the guide wire 786, even as the catheter 774 is retracted relative to the pusher 772 to release the stent 793.

As best seen in FIGS. 54-57, a distal end of the core member 776 includes an anchor member 792 for anchoring and retracting the stent 793 during deployment. The anchor member 792 includes a body 792A that forms a backstop surface 792D against which the stent 793 can be pushed.

Figure 54:
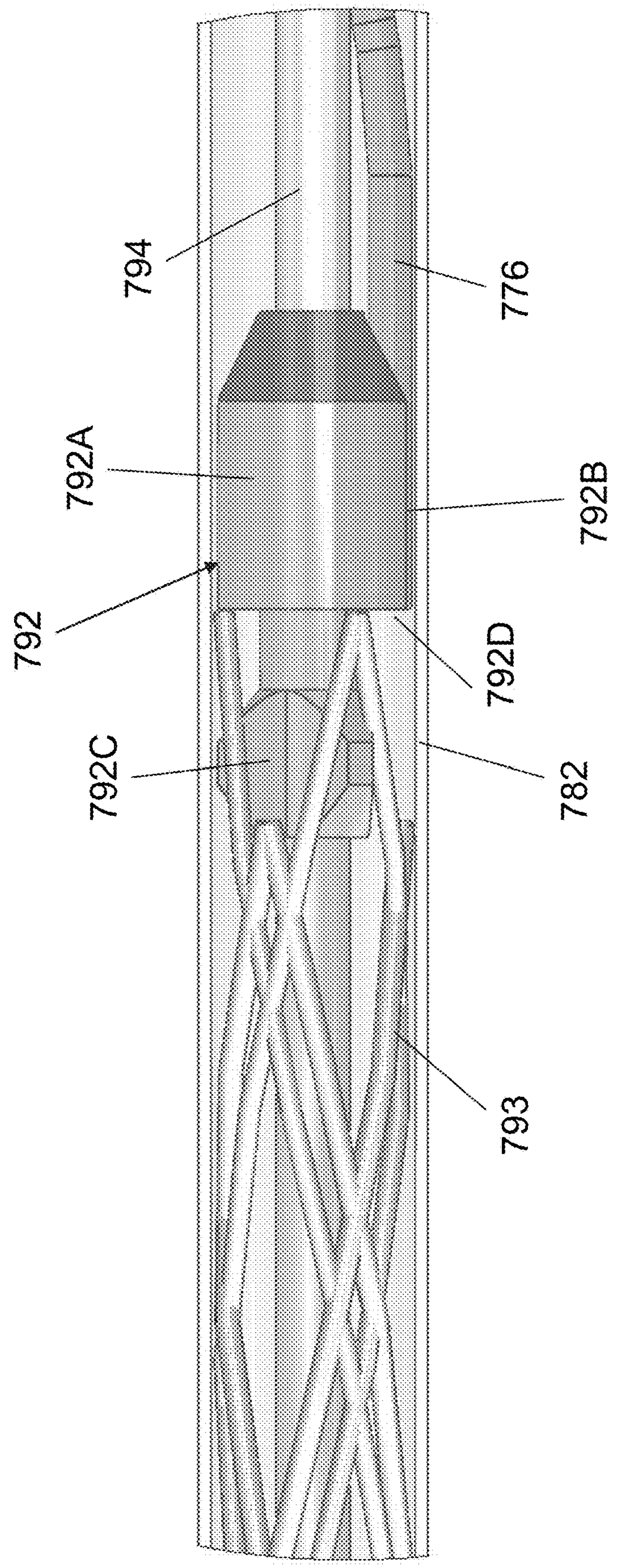
Figure 55:
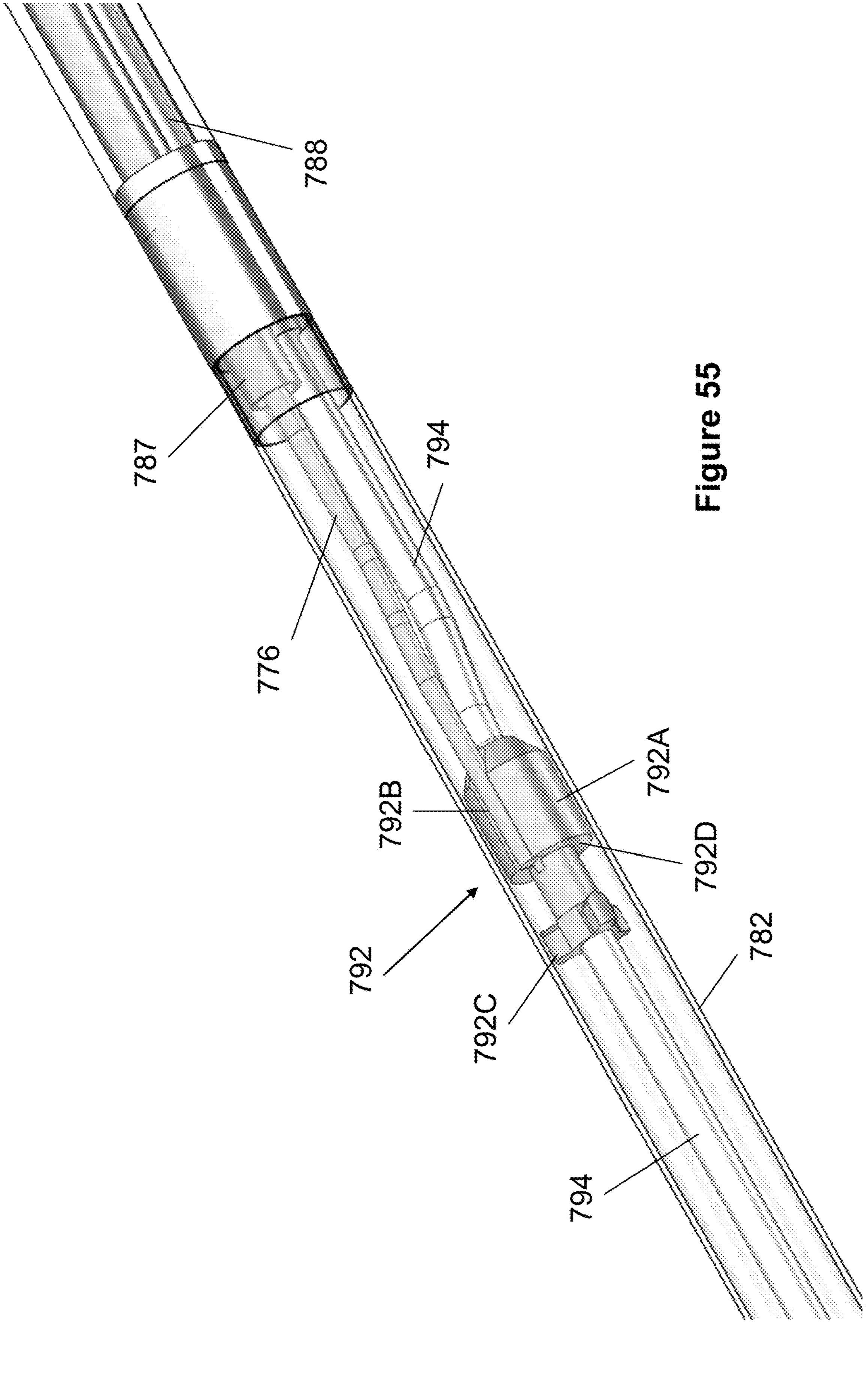
Figure 56:
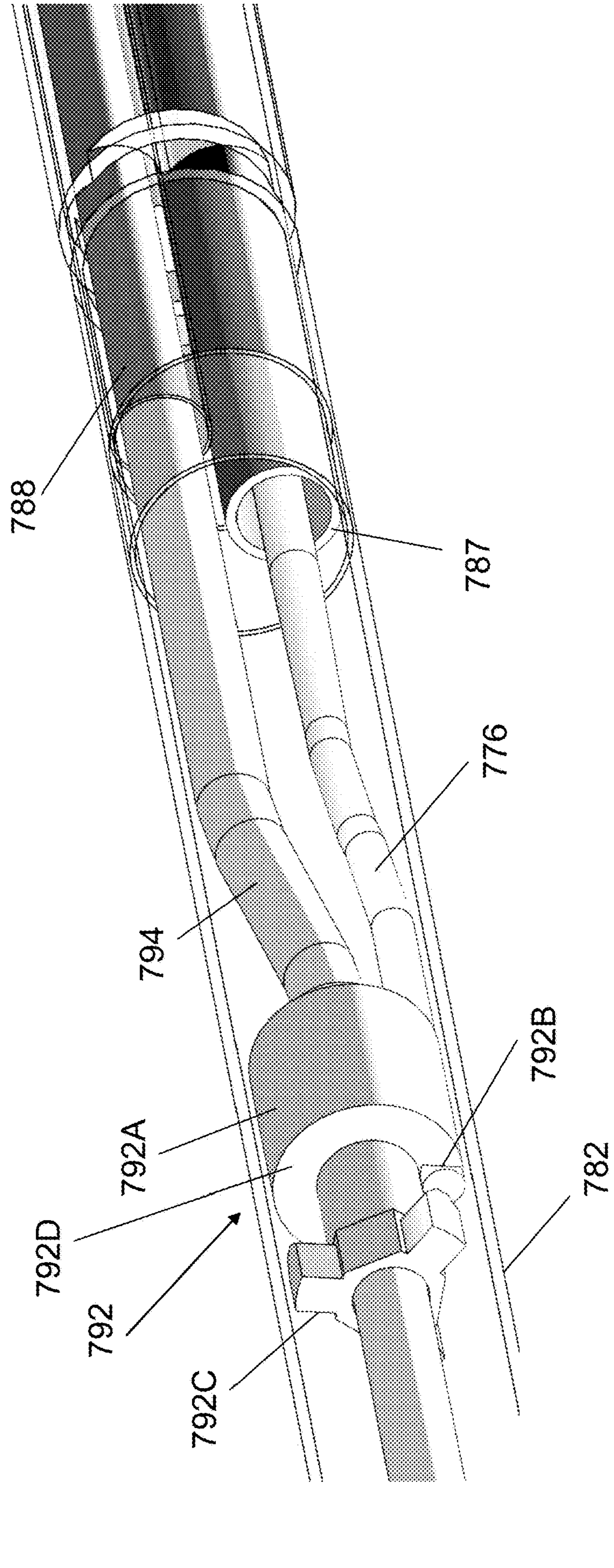
Figure 57:
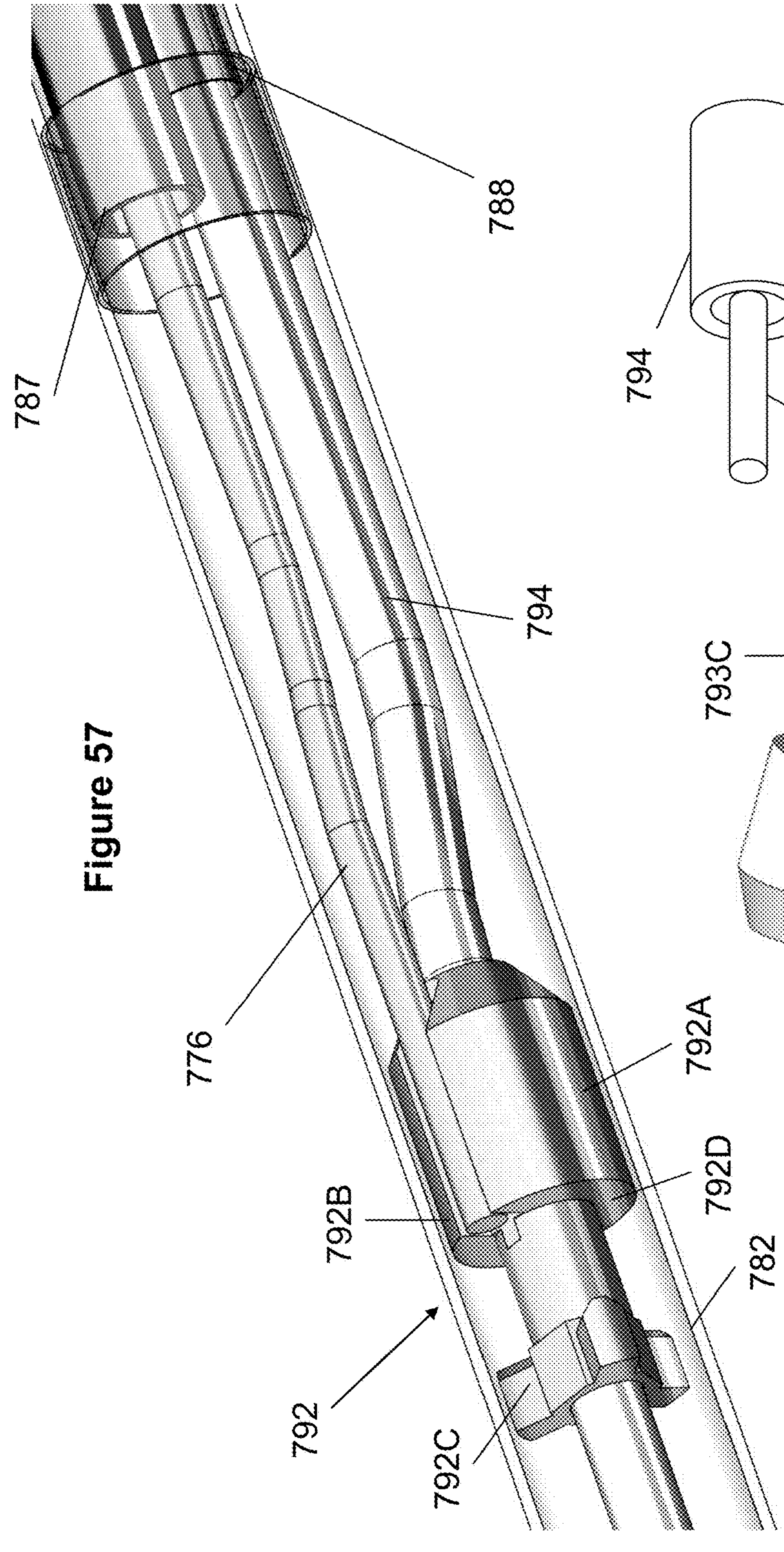

The stent 793 preferably includes a plurality of proximal loops that fit over a plurality of radially oriented posts 792C when the stent 793 is compressed on the pusher as seen in FIG. 54. For example, the stent 793 may have three loops and the anchor member 792 may have three posts 792C fixed at equidistant radial intervals from each other. During stent deployment, a physician may wish to retract the stent 793 so that it can be repositioned. As the pusher 772 is retracted or the catheter 774 is advanced, the posts 792C pull or anchor the end of the loops, causing the stent 793 to be pulled back into the outer tube 782 of the catheter 774.

In one embodiment, the posts 792C each have a generally flat distal surface and two angled or rounded proximal surfaces. In another embodiment seen in FIG. 59, the anchor 793 includes posts 793C having both distal and proximal surfaces that are angled toward each other (i.e., similar to a pyramid with a flat top surface).

Returning to FIGS. 54-57, the anchor 792 includes an elongated depression 792B that is sized to contain the core member 776. A distal end of the core member 776 is fixed in the depression 792B via known methods, such as welding or adhesives. As previously discussed, the core member passes through a core member passage 787 in the catheter 774, exits out of proximal port 780 and terminates with handle 778 on its proximal end. Hence, the core member 776 directly connects the anchor 792 and therefore the stent 793 to the handle 778, providing direct, positive, tactile feedback to the physician. Preferably, the anchor 792 is composed of metal to further enhance the tactile feedback felt by the physician.

Figure 60:
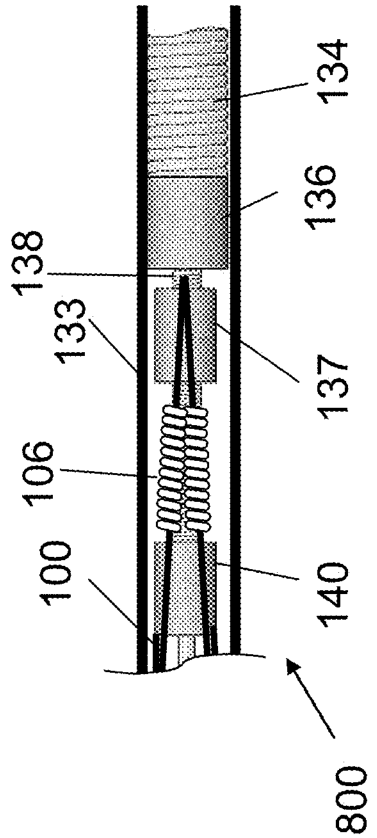
FIG. 60 illustrates another embodiment of a stent delivery pusher according to the present invention.

FIG. 60 illustrates another embodiment of a delivery pusher 130 that is generally similar to the delivery pusher 130 in FIGS. 7 and 8. However, delivery pusher 800 includes a third, middle marker band 137 located between marker bands 136 and 140. Preferably, the marker band 137 has a diameter similar to that of marker band 140 and is somewhat smaller in diameter than marker band 136. The stent 100 is preferable compressed over both markers 137 and 140 such that the proximal coils 106 of the stent 100 are positioned between and closely associated with the two markers 137 and 140. During deployment of the stent 100, a physician may wish to advance the pusher 800 relative to the outer catheter sheath 133. In this regard, the marker 137 distally pushes on the coils 106 at a location that may reduce the tendency of the stent 100 to buckle.

Figure 61:
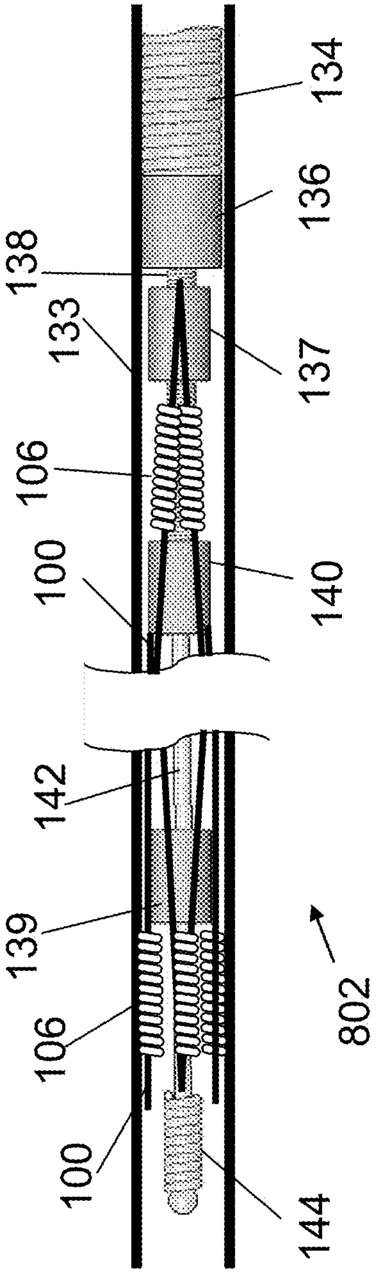
FIG. 61 illustrates another embodiment of a stent delivery pusher according to the present invention.

FIG. 61 illustrates another embodiment of a delivery pusher 802 that is similar to the previously described pusher 800. However, the pusher 802 also includes a marker 139 positioned near the coiled distal tip member 144. Preferably, the marker 139 is spaced proximally from the distal tip member 144 so as to allow space for the distal coils 106 of the stent 100. During stent deployment, the marker 139 may contact the distal coils 106 if the pusher 802 is advanced relative to the catheter sheath 133. In this regard, the marker 139 may be configured to initially push on the distal coils 106 until the distal end of the stent 100 exits the catheter sheath 133 and expands. From there, the marker 137 may push on proximal coils 106 until the remaining portion of the stent 100 has been pushed out of the catheter sheath 133.

In yet another embodiment similar to FIG. 61, the pusher may include markers 139, 140 and 136. In this respect, advancing the pusher relative to the sheath 133 may push the distal coils 106 and distal end of the stent 100 out of the catheter sheath 133.

It should be noted that one or more of any of the markers 136, 137, 139, and 140 from the previously described embodiments may alternately be composed of a non-radiopaque material. Additionally, one or more of any of the markers 136, 137, 139, and 140 from the previously described embodiments may be removed.

Figure 62:
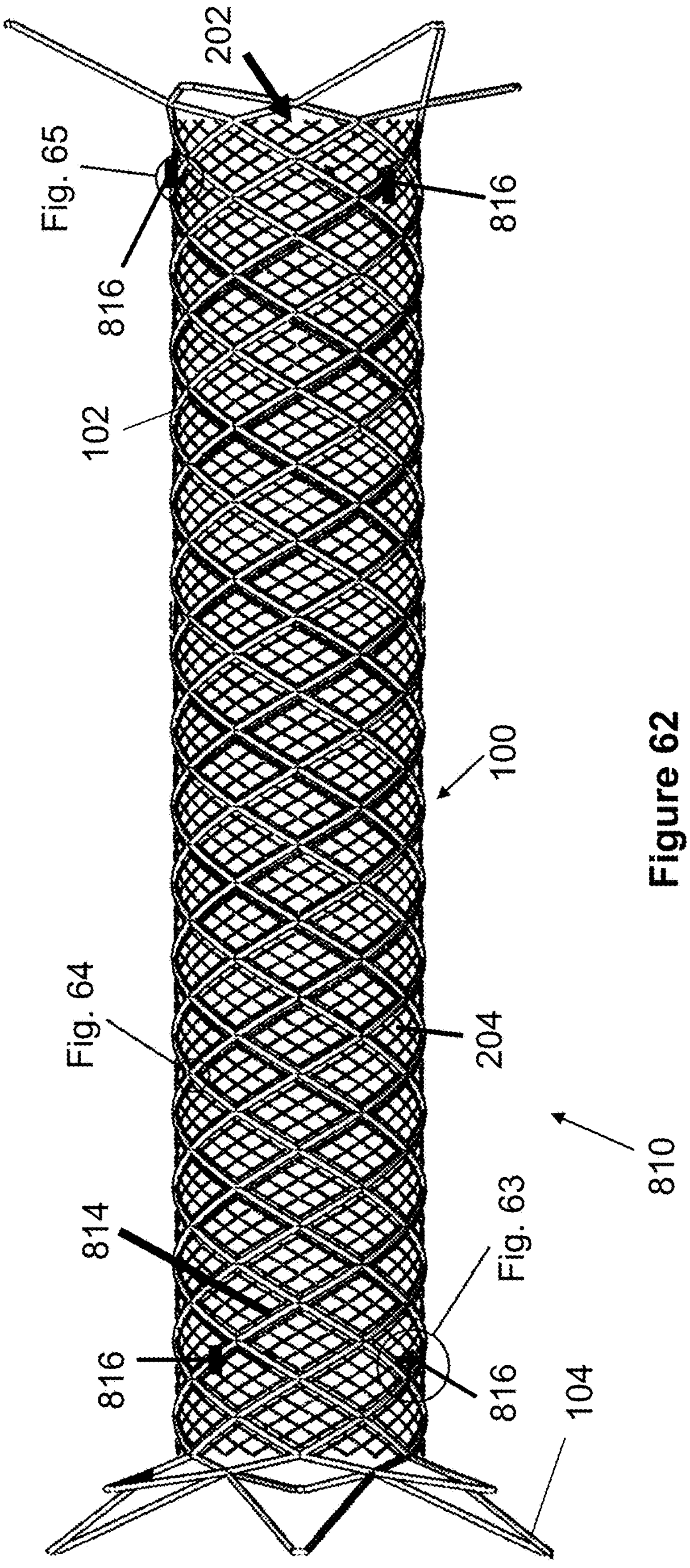
FIGS. 62-66 illustrate another embodiment of a dual layer stent according to the present invention; and, FIG. 67 illustrates another embodiment of a single layer stent having different sized wires according to the present invention.

FIG. 62 illustrates an embodiment of a flow diverting stent 810 which is similar to the stent 200 shown in FIGS. 12-14, including an outer anchoring stent layer 100 having six loops 104 on each of its distal and proximal ends, and a flow-diverting layer 202 that is located within the inner lumen or passage of the anchoring stent layer 100. However, the outer anchoring stent layer 100 and inner flow-diverting layer 202 are woven or braided so that their wires 102 and 204 have substantially the same pitch.

Woven stent layers tend to increase in length as they compress and decrease in length as they expand. When two woven stent layers have different pitches of braiding, the layer with the higher pitch typically elongates further and faster than a similarly sized layer having a relatively lower pitch braid. Therefore, to expand correctly, stent layers with different braid pitches can typically be attached at only one end of the stent.

In contrast, the layers 100, 202 of stent 810 have the same braid pitch which allows each layer to radially compress to the same increased length at the same rate, from similar expanded shapes, or radially expand to the same decreased length at the same rate. In other words, the layers 100, 202 maintain similar positions relative to each other as they simultaneously expand or contract. Since the layers 100, 202 remain in relatively the same positions in relation to each other, the layers can be constructed such that they have substantially no clearance between each other. This lack of clearance between layers may reduce or even prevent collapsing or buckling of the inner flow-diverting layer 202 within tortuous vessels. In one example, both the outer anchoring layer 100 and inner flow-diverting layer 202 may have a woven pitch of 40, 45, or 50 picks per inch.

As previously discussed, the layers 100, 202 of the stent 810 can be constructed to have substantially no clearance or gap between them. In addition to matching the pitch of the layers 100, 202, this close association of layers can be achieved by braiding and heat-setting the inner flow-diverting layer 202 on a rod or mandrel to have an outer diameter that is equal to the inner diameter of the inner diameter of the outer anchoring layer 100. This sizing provides a line to line fit of both layers, which can prevent physiological reactions like thrombosis.

Figure 63:
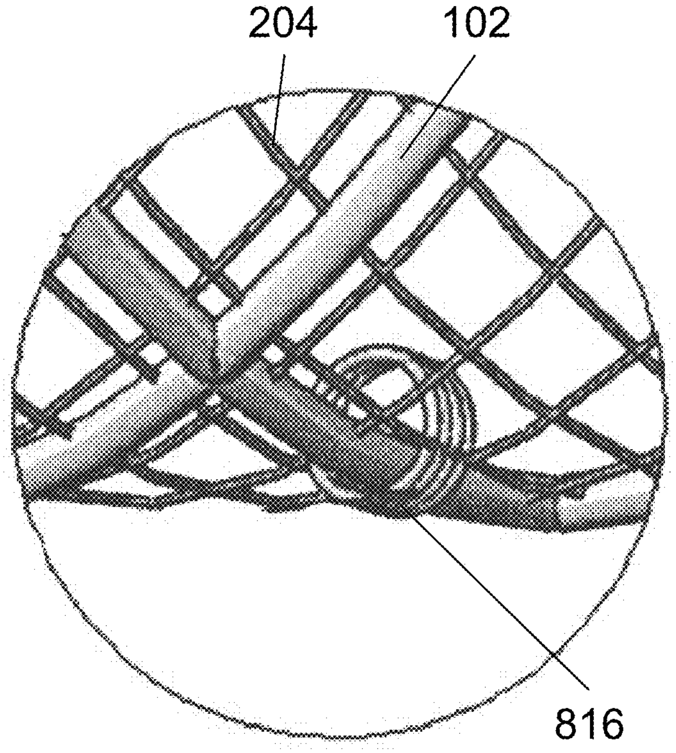
Figure 64:
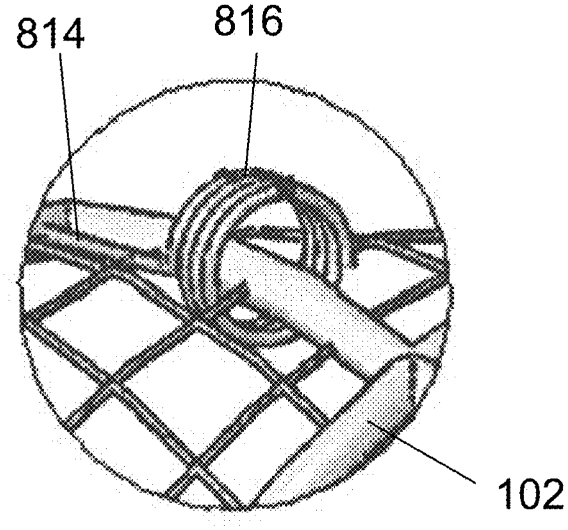

The close association of the layers 100, 202 can be further maintained by including one or more additional support wires 814 that are woven through both layers. For example, each end of a tantalum support wire 814 can be coiled around wire 102 near a distal and proximal end of the stent 810 and woven between the layers, as seen in FIG. 62 and the magnified areas of FIGS. 63 and 64.

Figure 65:
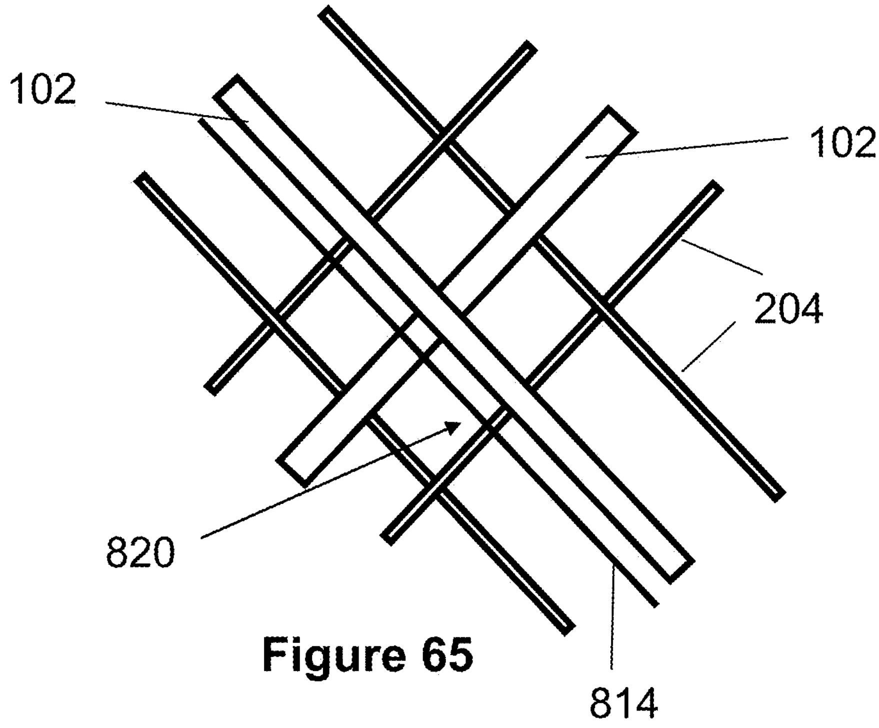
Figure 66:
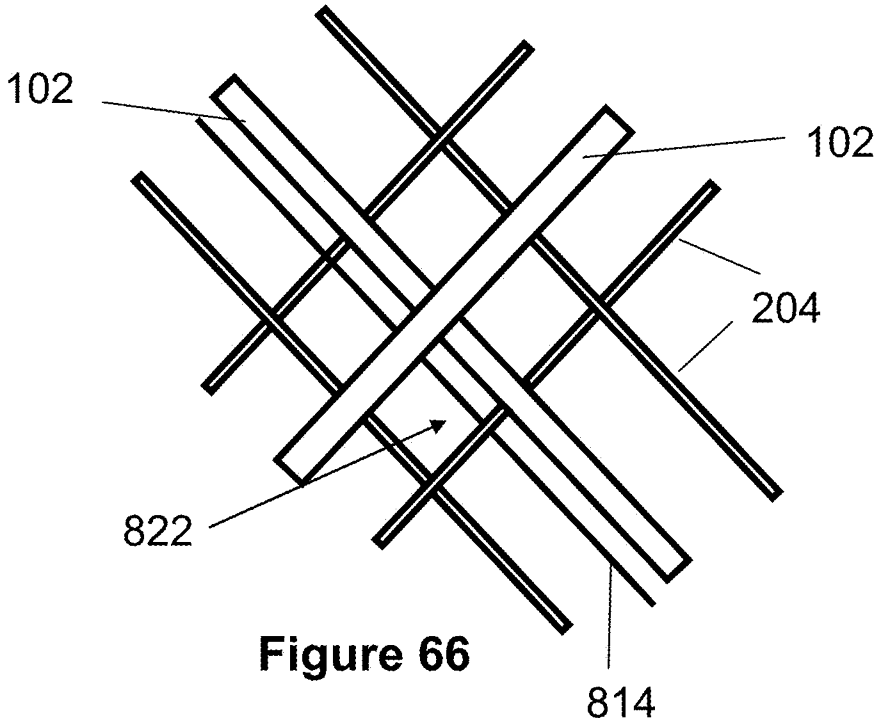

In the present example embodiment, three different support wires 814 are woven in a generally helical pattern through both layers 100, 202. For example, starting at one of the coils 816, the support wire 814 generally follows the curvature and position of each wire 102. As seen in FIG. 65, at areas where the wire 102 crosses over another portion of itself (i.e., radially outward), the support wire 814 follows a similar path over the crossing portion of wire 102, as well as over wires 204 (e.g., the area at 820). As seen in FIG. 66, at areas where the wire 102 passes underneath another portion of itself (i.e., radially inward), the support wire 814 also passes underneath the intersecting region of wire 102, but also further passes underneath the next intersecting wire 204, shown at area 822. Preferably, the pattern of FIG. 65 followed by FIG. 66 alternate with each other along the length of the stent 810. In this respect, the support wire 814 creates a radial shape that passes underneath wires 202 at regular intervals, thereby maintaining the two layers 100 and 202 against each other. By providing this additional support to maintain the layers, the stent 810 may particularly maintain the close association of layers 100 and 202 when deployed an a curved or tortuous vessel, such as a carotid artery.

In the present example embodiment, three support wires 814 extend substantially the entire length of the stent 810 and have equal radial spacing from each other. However, any number of support wires 814 can be used, such as 1, 2, 3, 4, 5, 6, 7, 8, 9. In another example embodiment, each support wire may extend from a location substantially near an end of the stent to a middle region of a stent, forming two sets of support wires 814 on each side of the stent 810. In another example embodiment, each support wire 814 may extend between each end of the stent 810, but may also include additional areas where the support wire 814 is coiled, such as at a middle region of the stent 810.

Figure 67:
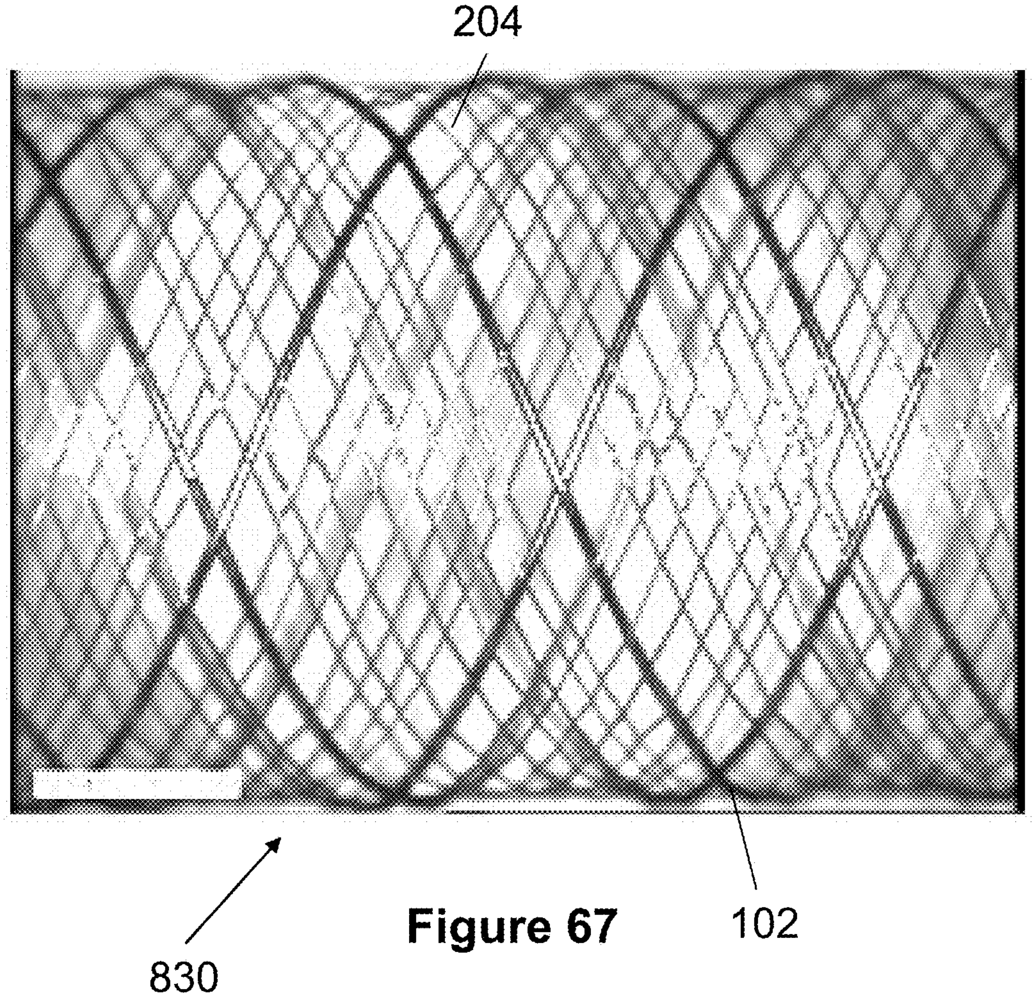

FIG. 67 illustrates another embodiment of a stent 830 having a single layer braided from larger wires 102 and smaller wires 204 that can have different sizes as described elsewhere in this specification. The wires 102 and 204 are preferably braided at the same braid angle, allowing them to expand and contract as similar rates and lengths. Preferably, all wires 102, 204 are woven according to the same braid pattern and the larger wire 102 is preferably separate by several wires 204 (e.g., each wire 102 is followed and preceded by 3 or 6 wires 204).

One advantage of this single layer stent 830 is that is can be braided on a braiding machine, rather than having portions or layers that are braided by hand. Unlike the previously described embodiments that utilize the single-wire stent layer 100, the single layer stent 830 may include multiple free ends of wires 102 after an initial braiding. Since these larger wires may have a tendency to curl and/or unravel, the free ends are preferably fixed together via welding, coils, tubes, adhesives, or similar methods. The free ends of wires 204 can be left free since they may not curl or unravel to the same extent as wires 102, or the ends of wires 204 can be similarly fixed or welded together. The stent 830 can be cylindrical or can be braided or heat-set to have a tapered shape.

It should be noted that any of the aspects of each stent or delivery system embodiment described in this specification can be combined with other aspects of other stent or delivery system embodiments described in this application. Therefore, while specific stent and delivery system embodiments have been shown, other combinations are contemplated in accordance with the present invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent, comprising:

a first plurality of wires having a first diameter; and, a second plurality of wires having a second diameter that is smaller than the first diameter;

wherein the first plurality of wires and the second plurality of wires are braided into a single layer tubular structure, are braided at a same braid angle, and are braided with a same braid pattern; and, wherein the braid pattern separates each of the first plurality of wires with a plurality of the second plurality of wires.

2. The stent of claim 1, wherein the single layer tubular structure has a radially contracted state and a radially expanded state; and wherein the first plurality of wires and the second plurality of wires radially expand at about a same rate and length when expanding between the radially contracted state and the radially expanded state.

3. The stent of claim 1, wherein a wire from the first plurality of wires is separated by 3 or 6 wires of the second plurality of wires as part of the braid pattern.

4. The stent of claim 1, wherein the stent is machine-braided.

5. The stent of claim 1, wherein ends of the first plurality of wires and the second plurality of wires are fixed together via welding, coils, tubes, or adhesives.

6. The stent of claim 1, wherein the single layer tubular structure has a uniform cylindrical shape or a tapered shape.

7. The stent of claim 1, wherein the single layer tubular structure comprises a plurality of loops around a perimeter of a proximal end of the single layer tubular structure, a distal end of the single layer tubular structure, or both the proximal end and the distal end of the single layer tubular structure.

8. The stent of claim 7, further comprising a plurality of coils; wherein each of the plurality of coils are located on a loop of the plurality of loops.

9. The stent of claim 7, wherein each of the plurality of loops are flared or biased to an outer diameter greater than an outer diameter of a main body portion of the single layer tubular structure.

10. The stent of claim 1, wherein the single layer tubular structure has a diameter within a range of about 3 mm and 10 mm.

11. The stent of claim 1, wherein the first plurality of wires and the second plurality of wires are further electropolished or etched to reduce the first diameter and the second diameter along only some areas of the single layer tubular structure.

12. A stent, comprising:

a first plurality of wires having a first diameter; and, a second plurality of wires having a second diameter that is smaller than the first diameter;

wherein the first plurality of wires and the second plurality of wires are braided into a single layer tubular structure and are braided at a same braid angle; and, wherein the first plurality of wires and the second plurality of wires are braided such that some of the second plurality of wires separates each of the first plurality of wires with a plurality of the second plurality of wires as part of a braid pattern.

13. The stent of claim 12, wherein the single layer tubular structure has a radially contracted state and a radially expanded state; and wherein the first plurality of wires and the second plurality of wires radially expand at about a same rate and length when expanding between the radially contracted state and the radially expanded state.

14. The stent of claim 12, wherein a wire from the first plurality of wires is separated by 3 or 6 wires of the second plurality of wires as part of the braid pattern.

15. The stent of claim 12, wherein the stent is machine-braided.

16. The stent of claim 12, wherein ends of the first plurality of wires and the second plurality of wires are fixed together via welding, coils, tubes, or adhesives.

17. The stent of claim 12, wherein the single layer tubular structure has a uniform cylindrical shape or a tapered shape.

18. The stent of claim 12, wherein the single layer tubular structure comprises a plurality of loops around a perimeter of a proximal end of the single layer tubular structure, a distal end of the single layer tubular structure, or both the proximal end and the distal end of the single layer tubular structure.

19. The stent of claim 18, further comprising a plurality of coils; wherein each of the plurality of coils are located on a loop of the plurality of loops.

20. A stent, comprising:

a single layer tubular structure means for causing a first plurality of wires having a first diameter a second plurality of wires having a second diameter that is smaller than the first diameter to expand at about a same rate and length between a contracted state of the single layer tubular structure and an expanded state of the single layer tubular structure.

* * * * *